United States Patent
Glensbjerg et al.

(10) Patent No.: US 10,458,896 B2
(45) Date of Patent: Oct. 29, 2019

(54) IMAGE FORMING CYTOMETER

(71) Applicant: ChemoMetec A/S, Allerød (DK)

(72) Inventors: Martin Glensbjerg, Brønshøj (DK); Johan Holm, Søborg (DK); Søren Kjaerulff, Hillerød (DK); Frans Ejner Ravn Hansen, Frederiksberg (DK)

(73) Assignee: ChemoMetec A/S, Allerød (DK)

( * ) Notice: Subject to any disclaimer, the term of this patent is extended or adjusted under 35 U.S.C. 154(b) by 103 days.

(21) Appl. No.: 14/893,780

(22) PCT Filed: May 28, 2014

(86) PCT No.: PCT/DK2014/050151
§ 371 (c)(1),
(2) Date: Nov. 24, 2015

(87) PCT Pub. No.: WO2014/191003
PCT Pub. Date: Dec. 4, 2014

(65) Prior Publication Data
US 2016/0103058 A1    Apr. 14, 2016

(30) Foreign Application Priority Data
May 28, 2013    (DK) ............................... 2013 70291

(51) Int. Cl.
*G06K 9/00*    (2006.01)
*G01N 15/14*    (2006.01)
(Continued)

(52) U.S. Cl.
CPC ..... *G01N 15/1434* (2013.01); *G06K 9/00127* (2013.01); *G06T 7/0012* (2013.01);
(Continued)

(58) Field of Classification Search
CPC ....... G01N 15/1434; G01N 2015/0065; G01N 2015/1006; G01N 2015/1438;
(Continued)

(56) References Cited

U.S. PATENT DOCUMENTS 4,786,165 A    11/1988   Yamamoto et al.
4,881,802 A    11/1989   Stankewitz
(Continued)

FOREIGN PATENT DOCUMENTS

DE    10239955    5/2004
EP    0501006 A2    9/1992
(Continued)

OTHER PUBLICATIONS

European Office Action dated Dec. 11, 2018; European Application No. 14 733 071.6-1001.

*Primary Examiner* — Nirav G Patel
(74) *Attorney, Agent, or Firm* — Dinsmore & Shohl LLP

(57) ABSTRACT

The present invention relates to methods and systems for image cytometry analysis, typically at low optical magnification, where analysis is based on detection of biological particles using UV bright field, dark field or one or more sources of excitation light. The system comprises illumination means (11, 112), a sample holder (100), a sample compartment (101), imaging means (120), collection means (121), light modulation means (122, 123), and detection means (130) with active detection elements (131).

25 Claims, 16 Drawing Sheets

(51) Int. Cl.
*G06T 7/00* (2017.01)
*G01N 15/00* (2006.01)

(52) U.S. Cl.
CPC ............ *G01N 2015/0065* (2013.01); *G01N 2015/144* (2013.01); *G06T 2207/10056* (2013.01); *G06T 2207/10064* (2013.01); *G06T 2207/30024* (2013.01)

(58) Field of Classification Search
CPC .......... G01N 2015/144; G06K 9/00127; G06T 2207/10056; G06T 2207/10064; G06T 2207/30024; G06T 7/0012
See application file for complete search history.

(56) References Cited

U.S. PATENT DOCUMENTS

| | | | |
|---|---|---|---|
| 6,707,555 B1 | 3/2004 | Kusuzawa et al. | |
| 6,710,879 B1 | 3/2004 | Hansen et al. | |
| 6,731,100 B1 | 5/2004 | Hansen et al. | |
| 6,809,324 B1 | 10/2004 | Schmidt | |
| 6,919,960 B2 | 7/2005 | Hansen et al. | |
| 7,068,365 B2 | 6/2006 | Hansen et al. | |
| 7,106,442 B2 * | 9/2006 | Silcott | G01N 15/1459 356/336 |
| 8,010,299 B2 | 8/2011 | Arnvidarson | |
| 8,081,312 B2 | 12/2011 | Hansen et al. | |
| 8,125,643 B2 | 2/2012 | Hansen et al. | |
| 8,259,300 B2 | 9/2012 | Arnvidarson | |
| 8,363,221 B2 | 1/2013 | Hansen et al. | |
| 8,432,550 B2 | 4/2013 | Hansen et al. | |
| 8,860,938 B2 | 10/2014 | Kjærulff et al. | |
| 8,906,697 B2 | 12/2014 | Glensbjerg | |
| 9,778,178 B2 * | 10/2017 | Yamada | G01N 21/49 |
| 2005/0259245 A1 | 11/2005 | Cemic et al. | |
| 2007/0121106 A1 | 5/2007 | Shibata et al. | |
| 2007/0190661 A1 | 8/2007 | Gudermann et al. | |
| 2009/0208072 A1 | 8/2009 | Selbel et al. | |
| 2010/0079762 A1 * | 4/2010 | Kusuzawa | G01N 15/1425 356/442 |
| 2010/0189338 A1 | 7/2010 | Lin et al. | |
| 2010/0189388 A1 | 7/2010 | Draser | |
| 2011/0285991 A1 * | 11/2011 | Dal Negro | G01N 21/253 356/301 |
| 2012/0195024 A1 | 8/2012 | Kawaguchi et al. | |
| 2015/0053872 A1 | 2/2015 | Kjaerulff et al. | |

FOREIGN PATENT DOCUMENTS

| | | |
|---|---|---|
| EP | 2348301 | 7/2011 |
| JP | 2006084233 A | 3/2006 |
| JP | 2007033381 A | 2/2007 |
| JP | 2007212201 A | 8/2007 |
| JP | 20082932 A | 1/2008 |
| WO | WO-2004048970 | 6/2004 |
| WO | 2011068764 A2 | 6/2011 |
| WO | WO-2011088014 | 7/2011 |
| WO | WO-2012096153 | 7/2012 |

* cited by examiner

B

C

D

E

F

G

B

C

D

E

B

C

G

H

I

J

K

IMAGE FORMING CYTOMETER

CROSS-REFERENCE TO RELATED APPLICATIONS

This application is the U.S. national phase of foreign application Serial No. PCT/DK2014/050151, filed May 28, 2014, which claims priority to foreign application Serial No. PA 2013 70291, filed May 28, 2013, the contents of which are incorporated herein in their entirety.

FIELD OF THE INVENTION

The present invention relates to methods and systems for image cytometry analysis, typically at low optical magnification, where analysis is based on detection of biological particles.

DESCRIPTION OF THE RELATED ART

Microscopy has been used for the analysis of biological material for a long time. In order to see an object in a microscope it is necessary that the object displays optical properties that differs from the optical properties of the background and this difference is called contrast. Biological particles are typically largely made up of water, contained within the cell membrane, which makes them inherently similar to their surroundings. The interior of the cell differs typically from the surrounding liquid by certain chemical constituents, such as proteins, DNA and RNA, some of which form "structure" which is of such size that it can potentially be visualised, for instance DNA packed into a cell nuclei. Biological particles, such as mammalian cells, yeast and bacteria are relatively small, typically less than about 20 μm in diameter, which can make them difficult to view in microscopy unless some advanced techniques are applied. Among such techniques are high magnification, phase contrast and UV microscopy and with the introduction of digital technology several image enhancement techniques have been introduced.

High magnification microscopy typically uses magnification of ×50 or more, which makes it possible to separate the minute structures which aids the visualisation and identification of the biological particles. Phase contrast microscopy exploits small differences in refractive index to produce an image with high contrast. UV microscopy uses absorbance properties of proteins and DNA, which absorb light at around 260 and 280 nm respectively. The absorbance of light is seen as contrast in the microscope. Further light of short wavelength makes it possible to separate smaller structures than is possible using light of longer wavelength since the maximum resolution of the microscope is dependent on the wavelength of the light. Such small structures in biological particles are typically the internal structures of a cell, such as a nucleus.

In assessment of biological particles by Image Cytometry it is of paramount importance to know the location of biological particles in the image. This is of course obvious when the task of analysing biological particles is the enumeration of particles in a sample but this is also the case in most any assessments concerning other properties of samples and/or cells. A necessary condition for the identification of any object in an image is that it is possible to establish conditions where there is a significant difference in the image of the object and that of the surrounding background.

Typical methods of microscopy are based on optical properties which do not modify the wavelength of light, such as difference in refractive index, reflectivity or attenuation, while methods such as fluorescence microscopy are based on shift in wavelength of light, typically brought about by quantum mechanical properties of matter.

In microscopy such difference is generally referred to as "contrast". There are several methods to produce contrast in microscopy, the two basic methods being Dark Field (DF) and Bright Field (BF) microscopy, where the intensity of the "Field" signal refers to the intensity of the background, that is the region of the image separating any objects which might be present. Therefore in DF the background is dark and the objects have higher intensity, contrary to BF where the background is luminous and the image of objects represents decrease in light.

When considering microscopy analysis of biological particles, such as biological cells both DF and BF microscopy methods render images of rather poor contrast. Therefore there are additional techniques which are widely used in the analysis of biological particles since they generally offer greater contrast in the images, such as phase contrast and fluorescence microscopy. Both methods have advantages as well as drawbacks when it comes to implementation for the identification of biological particles. Phase contrast microscopy requires specialised optical components, while fluorescence microscopy is limited by selectivity defined by the fluorophore system used, which either must be present in the particles or bound to the particles.

SUMMARY OF THE INVENTION

Present invention offers a simple, effective and reliable method to record images of biological particles with considerable contrast, which makes methods and system according to the invention particularly well suited for the identification of particles in Image Cytometry.

The present invention provides an image cytometer, comprising:
 a first light source configured for emitting light into a sample region;
 focusing means for forming collimated light and directing the collimated light from the first light source along an optical axis of the cytometer;
 a second light source comprising a first excitation light source configured for emitting excitation light into the sample region; and
 image forming means for forming an image of at least part of the sample region on an array of detection elements, wherein
  the sample region is located between the focusing means and the array of detection elements, and wherein
  the cytometer is able to be configured to be interchanged between a bright field mode, a dark field mode and a fluorescence mode, and/or wherein
  the first light source is configured for emitting light with a wavelength less than 400 nm, and/or wherein
  the excitation light is at an incidence angle relative to the optical axis so as to provide the fluorescence mode.

The present invention provides further an illumination system for an image cytometer, comprising:
 a first light source configured for emitting light;
 focusing means for directing the light from the first light source along an optical axis of the image cytometer and into a sample region; and a second light source comprising a first excitation light source configured for emitting excitation light and into the sample region, wherein the light from the first light source is configured for emitting light with a wavelength less than 400 nm.

Even further, the present invention provides a method for the assessment of at least one quantity parameter and/or one quality parameter of a biological sample, comprising:

applying a volume of the biological sample to a sample compartment having parallel wall parts defining an exposing area, the wall parts allowing light from an image cytometer to pass through the wall parts of the sample compartment, illuminating the sample compartment with light from the first light source, and exposing, onto a 2-dimensional array of active detection elements, light having passed through the sample compartment, thus recording an image of spatial light intensity information, illuminating the sample compartment with excitation light from the second light source, and exposing, onto the 2-dimensional array of active detection elements, fluorescent light having passed through the sample compartment, thus recording a fluorescent image of spatial light intensity information, processing both images in such a manner that light intensity information from individual biological particles are identified as distinct from light intensity information from the background, and correlating the results of the processing to the at least one quantity parameter and/or quality parameter of biological particles in the biological sample.

BRIEF DESCRIPTION OF THE DRAWINGS

FIG. 2A shows a graph that illustrates observed contrast.

FIGS. 2A, 2B, 2C, 2D, 2E, 2F, and 2G illustrate Bright-field images recorded using different wavelength of light.

DESCRIPTION OF THE INVENTION

Figure 1:
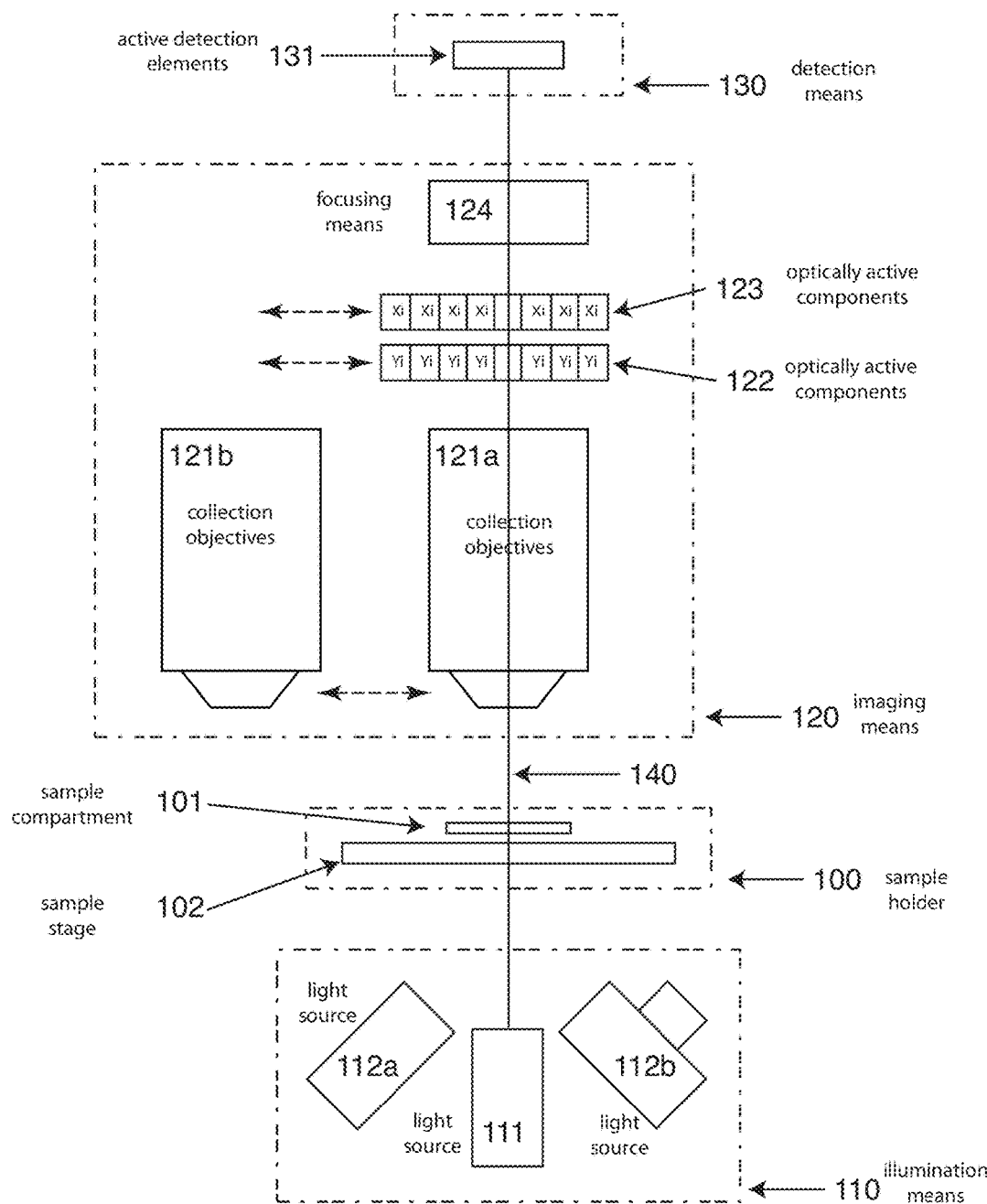
FIG. 1 illustrates an embodiment of an image cytometer according to the present invention.

One first effect of the image cytometer according to one embodiment is that the image cytometer is able to be configured to be interchanged between a bright field mode, a dark field mode and a fluorescence mode. In a preferred embodiment of the present invention, the first light source may provide the bright field light source and the dark field light source, such that only a single light source is required for the bright field mode and the dark field mode. The interchanging between the two modes may thus be obtained by interchanging means rather than changing of light source or optical means. Preferably the first light source is configured for emitting light with a wavelength less than 400 nm. In this perspective, the first light source may be regarded as an ultraviolet (UV) bright field light source. It has been found that an effect of using a UV bright field light source is that such illumination provides more details about the particles, and/or higher contrast in an image, in comparison to images recorded with light from a light source emitting light with a higher wavelength than 400 nm.

According to the present invention, the second light source may provide the fluorescence mode, and an effect of the present invention is that the fluorescence mode may be provided without moving the second light source or parts that may direct fluorescence light from the second light source. In other words, the fluorescence mode may be provided rapidly since there may be no movement of a fluorescence light source or no movement of parts that may direct fluorescence light. Preferably, the excitation light is at an incidence angle relative to the optical axis, the optical axis of the image cytometer being defined by the axis between the sample region and the array of detection elements, so as to provide the fluorescence mode. It has been found that one effect of such a setup is that the intensity of exposed excitation light onto the detection elements may be reduced significantly.

Attenuation Means and Modulation Means

In preferred embodiments of the present invention, the image cytometer further comprises attenuation means, such as an optical filter such as to attenuate the light intensity in one or more predefined wavelength band(s), preferably where attenuation means are placed at a predetermined plane along the optical axis. Even further, the image cytometer may further comprise modulation means, such as a spatial modulation means, preferably where modulation means are placed at a predetermined plane along the optical axis. In some embodiments of the present invention, the attenuation means and/or the modulation means is/are placed in the light path between the first light source and the sample region. Preferably, the attenuation means and/or the modulation means is/are placed in the light path between the sample region and the array of detection elements. More preferably, the modulation means are placed in or close to the focal plane of collimated light transmitted through the sample region towards the detection elements along the optical axis.

It has been found that there are many effects of having modulation means placed in or close to the focal plane of the collimated light transmitted through the sample region are many. First of all, the contrast, such as at high spatial frequencies, may be improved compared to an arrangement without modulation means at this position. Secondly, since the focal plane of the collimated light may be the aperture stop of the image-forming device, the modulation means may yield extended depth of field. Thirdly, the modulation means may allow only the light refracted or dispersed by particles in a sample in the sample region to reach the detection elements and eliminating light emitted directly from the light source. By an arrangement where the modulation means is placed in or close to the focal plane of the collimated light transmitted through the sample region it may be possible to realise an image cytometer that has the flexibility of recording high contrast bright field or dark field images, or the combination of the two, simply by placing or removing a suitable modulation.

In some embodiments of the present invention, two or more of the attenuation means and/or the modulation means is/are mounted in interchanging means that allow removal or interchanging of the attenuation means and/or modulation means. The interchanging means may for example comprise a rotating unit, such as a filter wheel. The two or more interchanging means may be such that none, one, two or more attenuation and/or modulation means can be positioned along the optical axis at the same time. An effect of having two or more interchanging means may be that these allow for combined effects of modulations means, attenuations means or both means. Another effect may be that two or more interchanging means may interchange the attenuation means and/or the modulation means more rapidly than a single interchanging means having the same number of attenuation means and/or modulation means, for example since such interchanging means may be smaller, and able to rotate faster than the single interchanging means.

In some embodiments of the present invention, at least one modulation means may be partly opaque or partly transparent. The attenuation and/or the modulation means may likewise be partly opaque in some part(s) and partly transparent in different part(s), preferably where one or more of the parts is/are circular in shape. Accordingly, part of at least one modulation means may be partly opaque and another part of the modulation means may be partly transparent. Preferably, the attenuation means may attenuate light by a predetermined factor, such as less than $10^{-3}$, such as less than $10^{-4}$, such as less than $10^{-5}$, or such as less than $10^{-6}$.

In a preferred embodiment of the present invention, the modulation means comprises an obstruction configured for the dark field mode, preferably substantially attenuating collimated light passing through the sample region. In another preferred embodiment of the present invention, the modulation means comprises an aperture configured for the bright field mode, preferably substantially attenuating uncollimated light emitting from the sample region. It may be achieved by interchanging of the obstruction and the aperture, that the interchanging between the bright field mode and the dark field mode is possible. Interchanging between a bright-field mode and a dark-field mode may thus be realised by modulation means, preferably by inserting and/or interchanging modulation means located between the sample region and the array of detection elements.

In another preferred embodiment of the present invention, the modulation means comprise phase contrast microscopy modulation means. Accordingly, the modulation means may constitute phase contrast microscopy modulation means and the substantial wavelength of the light emitted by the first light source is of a narrow waveband, preferably where the width of the waveband is less than 50 nm.

First and Second Light Sources

In optical setup, it may be accepted that a perfectly collimated is not always possible to obtain, and the collimated light from the first light source may deviate from collimated light with a deviation angle less than 10 degrees, more preferably less than 5 degrees.

In embodiments of the present invention, the wavelength from the first light source is between 200 nm and 700 nm. Preferably, the wavelength from the first light source may be between 300 nm and 395 nm. Even more preferably, the wavelength from the first light source may be between 320 nm and 380 nm. Most preferably, the wavelength from the first light source may be between 350 nm and 380 nm.

The excitation light from the second light source may have a wavelength substantially different from the wavelength of light from the first light source. Preferably, the incidence angle of the excitation light may be between 10 and 80 degrees, preferably between 20 and 60 degrees, and more preferably between 30 and 50 degrees. Alternatively, the incidence angle of the excitation light may be 90 degrees. In another alternative embodiment of the present invention, the incidence angle is between 110 and 180 degrees, preferably between 120 and 160 degrees, and more preferably between 130 and 150 degrees.

Focusing Means

In a preferred embodiment of the present invention, the focusing means comprises a lens, whereas in another equally preferred embodiment of the present invention, the focusing means comprises a curved mirror.

Additional Light Sources

In some embodiments of the present invention, the image cytometer further comprises an additional light source, such as a third or fourth or fifth or sixth light source, preferably where the additional light sources are excitation light sources. The light source(s) may be a light emitting diode and/or a diode laser and/or a laser such as tuneable solid-state light source(s) and/or a tuneable light emitting diode. The tuneable solid-state light source may be a tuneable laser diode.

Optical Means and Detection Elements

In preferred embodiments of the present invention, the light source(s) is/are optically connected to optical means configured for providing light with a substantially uniform intensity across the sample region and/or across a region imaged by the array of detection elements. The optical means may comprise an array of micro lenses. Alternatively, The optical means may comprise an array of cylindrical micro lenses, preferably it may comprise two arrays of cylindrical micro lenses with substantially perpendicular orientation of the cylindrical lenses. The array of detection elements may be an array of CCD or CMOS sensor elements.

Exposures

According to the present invention, the light source(s) is/are configured for emitting light in duration less than 1 second, preferably for less than 0.1 second. Preferably, the light source(s) is/are configured for emitting light in duration between 0.0001 and 0.1000 second, preferably between than 0.0001 and 0.0500 second. However, in some situations such as when high sensitivity is required in fluorescence imaging, the light source(s) may be configured for emitting light in duration for more than a 1 second, such as for more than 2 seconds, such as for more than 3 seconds, such as for more than 4 seconds, such as for more than 5 seconds, such as for more than 6 seconds, such as for more than 7 seconds, such as for more than 8 seconds, such as for more than 9 seconds or such as for more than 10 seconds.

Light Blocking

In one embodiment of the present invention, light from the excitation light source may substantially be eliminated from reaching the entrance of the image forming means by selectively removing rays of light from the beam of excitation light. The rays may be selectively removed by placing one or multiple obstructions in the beam of excitation light, preferably where the beam of excitation light is substantially collimated in the plane where the obstruction is placed.

Image Forming Means

In a preferred embodiment of the present invention, the image forming means is configured for providing a depth of field that is more than 5 µm, such as between 10 µm and 150 µm. In this way, the sample region may be in focus in the depth of field such that the image forming means and/or the array of detection elements may not need to be moved in order to acquire a sharp image of a sample in a sample region, for example when the sample has particles positioned at different depths. However, in some embodiments of the present invention, the image forming means and/or the array of detection elements and/or the sample compartment may be configured for moving such that image forming means and/or the array of detection elements may be placed at an optimal position relative the sample. One sample or a part of a sample may for example be in focus in one configuration, but when changing to another sample or to a different part of a sample, the other sample or the different part of the sample may then not be in focus, and it may thus be required to either move the sample and/or the image forming means and/or the array of detection elements.

In preferred embodiments of the present invention, the image forming means is configured for transmitting light in the wavelength region of between 200 nm and 1000 nm, more preferably in the wavelength region of between 350 nm and 1000 nm, more preferably in the wavelength region of between 350 nm and 850 nm.

In several preferred embodiments of the present invention, the image forming means comprises a microscope objective. The image forming means may be configured for providing a linear enlargement of the sample. Preferably, the linear enlargement is smaller than 20:1. The linear enlargement may also be in the range from 1:1 to 20:1, preferably in the range from 1:1 to 10:1, more preferably in the range from 1:1 to 4:1.

In several preferred embodiments of the present invention the image cytometer is configured with means which allow two or more image forming means to be interchanged between recording of images. The purpose of interchanging imaging means is preferably to change the optical properties of the image cytometer, such as to change linear magnification of the image and/or to change the depth of field of view. Often the selection of imaging means is made on the basis of a priori know properties of a sample, but in several preferred embodiments of the present invention the selection of imaging means is made on the basis on results of an assessment of the sample being analysed.

Sample

The sample region may comprise a sample such as a biological sample. The sample may be in a sample compartment.

Illumination System

According to the present invention, the illumination system may be for providing the required light sources to an image cytometer, being a bright field light source, and a fluorescence light source. In a preferred embodiment of the present invention, the focusing means in relation to the illumination system is for forming collimated light from the first light source. Furthermore, the excitation light may be at an incidence angle relative to the optical axis. The illumination system may additionally have any of the features from the image cytometer as previously described.

Cytometry Method

In one aspect of the present invention, there is provided a method for the assessment of at least one quantity parameter and/or at least one quality parameter of biological sample, comprising applying a volume of the sample to a sample compartment having parallel wall part defining an exposing area, the wall part allowing light from a first light source to pass through the wall parts of the sample compartment, exposing, onto an array of active detection elements, light having passed through the sample compartment, thus recording an image of spatial light intensity information, processing the image in such a manner that light intensity information from individual biological particles are identified as distinct from light intensity information from the background, and correlating the results of the processing to the at least one quantity parameter and/or the at least one quality parameter of biological particles in a liquid sample.

The present invention relates to methods and systems for the assessment of quality and/or quantity parameter of biological samples, including optical interaction with the sample. The optical interaction with the sample preferably causes alteration in intensity and/or direction of light as a result of interaction with a biological sample, or particles in said biological sample, some of the preferred interactions being one or more of the following; reflection, refraction, diffraction, interaction, scattering or absorbance.

In preferred embodiments of the present invention the biological sample being assessed is contained in a sample compartment. A preferred property of the sample compartment is to define a boundary of the sample. Another preferred embodiment of the present invention is where the wall part of the sample compartment is the bottom of an open container. In several embodiments the sample compartment the boundary is formed by a transparent wall part defining either bottom or top of the sample, while in other equally preferred embodiments the sample compartment is formed by two transparent wall parts, where the sample is placed in between the wall parts, defining the thickness of the sample being assessed.

In one preferred embodiment of the present invention the biological sample being assessed is a suspension of biological particles. Such suspension of biological particles can be a portion of a larger sample volume where the purpose of the assessment can be to determine or estimate the property of the larger sample volume. In another equally preferred embodiment, the biological sample is a sample of cells grown and/or growing on a substrate. Alternatively, the sample may be a liquid sample. In some preferred embodiment the substrate is in suspension, while in other equally preferred embodiment such substrate is, or can become, an integrated part of the sample compartment. Generally it is preferred that substrate placed in the sample compartment is substantially transparent and in many preferred embodiments the transparent substrate plate is a wall part of the sample compartment.

In preferred embodiment of the present invention the assessment of at least one quantity parameter and/or at least one quality parameter of biological sample is the analysis of individual cells. Such individual cells are often isolated, either in suspension or on a substrate, but such individual cells can also be in a clump of cells, such cells adhering to each other. In other preferred embodiments of the present invention the assessment of at least one quantity parameter and/or at least one quality parameter of biological sample is the analysis of bulk of cells, such as a tissue sample.

In several most preferred embodiments of the present invention the first light source is a light emitting diode (LED) and/or a diode laser and/or laser. Several of the properties of LED's and laser diodes offer substantial advantages in the design and operation of system according to the present invention, such as small physical size and power efficiency. In many preferred embodiments of the present invention the wavelength of the light from the first light source is less than 400 nm. It is often preferred that the wavelength of the light from the first light source is between 200 nm and 400 nm, such as between 300 nm and 395 nm. It has surprisingly been found that the use of light of short wavelength offers substantial improvement in the assessment of biological particles according to the present invention and light in wavelength bands such as 200 nm to 250 nm, 200 nm to 300 nm, 250 nm to 350 nm, and 320 nm and 380 nm are all preferred.

Often the biological particles being assessed are sensitive to light, to a degree where it can alter the properties of the particles, and one preferred method to reduce the effect of the light is to limit the length of time the sample is exposed to the light is to limit the time that the light source emits light onto the sample, preferably where the duration of illumination of light from the light source is less than 1 second, more preferably where it is less than 0.1 second. In other equally preferred embodiments illumination period is between 0.0001 and 0.1000 seconds, such as between 0.0001 and 0.0500 seconds. Expressed in energy, it is preferred that the sample is illuminated with 200 nJ/mm$^2$ or less, such as 100 nJ/mm$^2$ or less, preferably 50 nJ/mm$^2$ or less, such as 20 nJ/mm$^2$ or less during exposure.

One preferred method for the assessment of biological particles, according to the present invention, is based on recording an image of spatial light intensity information from the volume of sample where signal from individual biological particles is attenuated light intensity signal relative to light intensity from the background. The attenuation can be brought about by one or several of the following, reflection, refraction, diffraction, interference, absorption, scattering. In these embodiments the light relating to a biological particle is lower in intensity than the signal from the background and on the bases of this it is possible to process the image in a manner where the signal from individual cells and signal from the background are distinct from each other, preferably where the signal from the particle is substantially less than the signal from the background, preferable signal from the background in close spatial proximity to the particle.

In several preferred embodiments the attenuation of light is caused by the scattering of light, such scattering originating in processes such as refraction and/or reflection of light. Further in these and other preferred embodiments attenuation is caused by the absorption of light, such absorption being caused by chemical constituents of the biological particles under assessment and/or from other chemical constituents which are intentionally added to the sample. Accordingly, absorption may be caused by a reagent added to the sample. In embodiments according to the present invention attenuation of between 5% and 70% of the light associated to biological particles, relative to the intensity of signals from the background, is realised. In other equally preferred embodiments the attenuation of light associated to biological particles relative to light from the background is of between 50% and 90%.

In other equally preferred embodiments of the present invention signal from individual biological particles is enhancement, e.g. observed increase in light intensity signal relative to light intensity from the background. This can be caused by processes such as scatter, interference, reflection and refraction, typically in combination with focusing or other alteration of the light signal, the enhancement being the result of spatial re-distribution of light. In these embodiments the light relating to a biological particle is higher in intensity than the signal from the background and on the bases of this it is possible to process the image in a manner where the signal from individual cells and signal from the background are distinct from each other, preferably where the signal from the particle is substantially higher than the signal from the background, preferable signal from the background in close spatial proximity to the particle.

In yet other highly preferred embodiments of the present invention the recorded image of light intensity from biological particle comprises signals relating to biological particles, such images comprises change in light intensity information which is a combination of attenuation and enhancement of light intensity relative to the light intensity from the background.

An often preferred method of the present invention, which generally has the effect of increasing the contrast in the recording of light intensity information, is to modulate light transmitted or scattered through the sample. Preferably such modulation corresponds to spatial difference in light property at a predetermined plane in the light-path from the light source to the array of active detection elements. Such modulation is typically brought about through the use of modulation means, such as means that are opaque or substantially opaque, or transparent, preferably where the degree of transparency, e.g. attenuation is a predetermined property. Preferably such modulation means are implemented as a combination of opaque and transparent means thus the modulation means being opaque at predetermined locations, or regions, while it is transparent at other predetermined locations, or regions. Two preferred implementations of modulation means are firstly an opaque disk with a hole in its centre and secondly an opaque disk with diameter which is substantially less than the diameter of the parallel beam of light. When these two modulations means are used in combination then the dimension of the centre hole in the first means are similar or identical to the dimension of the disk in the second means. Preferably the predetermined location of opaque and/or transparent regions corresponds to an image of the light source at an optical plane in the vicinity of the location of the modulation means. Preferably such modulation means have different effect on light transmitted through the sample, and light being transmitted through a biological particle. Typical preferred location of modulation means are close to a focal plane of parallel light entering the collection objective of the imaging system.

Typically preferred properties of modulation means are those which alter the light passing through the modulation means, such as; change in phase, change in intensity, e.g. attenuation, masking of light, e.g. blocking of light. Modulation means preferably include one or several of these properties.

In may preferred embodiments modulation means are placed along the optical axis at location between the light source and the sample, while it is equally preferred to place modulation means at location along the optical axis between the sample and the array of active detection elements. Still may preferred embodiments include modulation means on both sides of the sample, along the optical axis. In embodiments included modulation means only at location along the optical axis between the sample and the array of active detection elements, the light from the light source is substantially parallel as it traverses the sample, preferably also the light intensity of such parallel light is substantially even across the portion of the sample being imaged by the array of active detection elements.

When optical components such as lenses are used to focus light from the sample compartment onto the array of active detection elements, parallel light transmitted through the sample compartment is often focused at a plane along the optical axis. Under these conditions it is often preferred to place modulation means at, or close to, such focus plane. In preferred embodiments light which has interacted with a biological particle, causing it for instance to be deflected, refracted and/or scattered, enters the collection objective of the imaging system. Further it is often preferred that the properties of the modulation means, such as opaque and transparent properties, are arranged to substantially follow the shape of the image of the light source at this focus plane. Often preferred properties and form of the modulation means is a difference in net effect of light transmitted through the sample compartment and light transmitted through a biological sample.

In embodiments including modulation means it is generally preferred to use light source that produce light consisting of a predetermined waveband of light, preferably where the waveband is substantially narrow, such as no more than 50 nm, preferably even less than 30 nm in width, such less than 20 nm. Further it is typically preferred to use light at predetermined wavelength, preferably where the wavelength of the light is predominantly less than 400 nm, such as between 250 nm and 400 nm, more preferably between 300 nm and 390 nm.

Preferred embodiments of the present invention include modulation means arranged in a manner which produces a phase contrast image, but under conditions where the wavelength of the light transmitted through the sample compartment is less than 400 nm.

Several preferred embodiments of the present invention include modulation mean that can be placed or removed from the light path, often preferably where two or more different modulation means are included. Accordingly, the two or more images of spatial light intensity may be recorded where two or more substantial different modulation means are applied. In such embodiments, where it is possible to alter the light path by including or omitting modulation means it is preferred to record two or more images of light intensity information from light transmitted through the sample compartment. Accordingly, the two or more images of spatial light intensity information, recorded using the first light source, may be used in the processing of light intensity information.

In a preferred embodiment light from a light source passed through the wall part of the sample compartment has general orientation that is substantially perpendicular to the surface of the wall part. In another preferred embodiment of the present invention, the light from the light source is substantially parallel as it passes the sample. In yet another preferred embodiment of the present invention, the collimated light having passed the sample is substantially focused to a plane located between focusing means and array of detection elements where modulation means are placed substantially in the focus plane. As light from a light source is preferably guided by the use of one or more optical component(s) such as a lens(es) and/or mirror(s), this orientation can be regarded as the optical axis of the light source and in that context the optical axis of the light source is substantially perpendicular to the surface of wall part. Further in several embodiments it is often preferred that the wall parts of the sample compartment is substantially perpendicular to the direction of view of the array of active detection elements. Similarly, as light is generally focused onto the array of active detection elements through the use of optical components such as lens(es) and/or mirror(s), this corresponds to that the optical axis of the array of detection elements is perpendicular to the wall parts. Thus several preferred embodiments of the present invention comprise a light source, sample compartment and array of active detection elements that are all substantially located on a single axis, such that the optical axis of a light source and the array of detection elements are substantially on a single axis, this axis passing through the sample compartment such that its wall parts are substantially perpendicular to this common axis.

Many highly preferred embodiments of the present invention include two or more light sources for the illumination of the sample. The two or more light sources typically differ in properties, such as arrangement of optical axis or wavelength. One preferred embodiment of the invention including two or more light sources is where a light from a second light source is passed through wall part of the sample compartment, where the second light source is arranged in a manner such that the main direction of light enters through wall part defining an exposing area of the sample compartment at an angle, preferably at an angle of between 10 and 80 degrees relative to perpendicular. Such arrangement offers typically advantage when two or more light sources are mounted at a substantially permanent location, in particular when more than two light sources are to be mounted. Further it has been found that such angular arrangement can reduce intensity of background light signal. Further, several preferred embodiments of the present invention include three or more, such as four light sources illuminating and/or passing light through the wall parts of the sample compartment. Other equally preferred embodiments include more than four light sources, such as five light sources. As the increasing number of light sources offer the possibility of performing an assessment of biological particles, where the processing is based on plurality of light intensity information, embodiments including six, seven, eight or even more than eight such as ten individual light sources are preferred.

Here, and elsewhere in the present discussion, the term "main direction of light" can be interchanged with the term "optical axis", which typically is formed by arranging a light source, or another active component such as an array of active detection elements, in combination with optical means such as one or more and/or mirror(s), (es), irrespective of the function of the lens(es) and/or mirror(s) whether it be for collimation, focusing or dispersion. The optical axis of such a system generally has an axis of symmetry.

In preferred embodiments of the present invention two or more individual light sources emit substantially identical light, for instance with respect to wavelength, preferably in situation such as where such two or more light sources are operated in substantial synchronisation and thus increasing the total light energy emitted, and/or extending the illuminated area of the sample compartment, and/or assuring more homogeneous light intensity illumination of at least a part of the sample compartment. In these but also in other equally preferred embodiments of the present invention two or more individual light sources emit substantially different light, for instance with respect to wavelength, preferably in situation such as where such two or more light sources are operated independently, such as only one such light source being turned on at a time, or such that only the light of one such light source is illuminating the sample compartment at a time. One preferred property of such two or more light sources emitting different light is that at least one of such light sources give rise to fluorescence, preferably where such fluorescence intensity information is used in combination with attenuated light intensity information for the purpose of assessing at least one quantity parameter and/or at least one quality parameter of biological sample.

In several preferred embodiments, all the light sources are located at the same side of the sample compartment. In such embodiments it is often preferred that such light sources are located at the opposite side of the sample compartment from the array of active detection elements.

Often it is preferred that two or more light sources are arranged in such a manner that light sources giving rise to fluorescence are placed at an angle to the wall parts of the sample compartment, such that the optical axis of the light source are substantially not perpendicular to the wall parts of the sample compartment. One preferred advantage of such an arrangement is the increase in the ratio of the intensity of fluorescence light emitted from biological particles to the intensity of light from the background, often termed Signal to Background (S/B). Light from the background, where background typically is/are region(s) in the image of light intensity information outside any biological particle of interest, can originate from of a number of sources and/or phenomena some of which are directly related to the properties of the light source, such as the orientation of the light source relative to the optical axis of the array of detection elements. Another equally preferred advantage of arranging a light source at an angle to the wall parts of the sample compartment is that it is possible to locate a number of light sources at a fixed position relative to the sample compartment, thus allowing illumination of the sample compartment with light from two or more light sources without use of mechanical means. Preferred advantage of such properties is/are more simple construction of a system and/or the ability to operate the system faster, when the task is to illuminate the sample in the sample compartment with two or more different wavelengths in sequence. Further it has been found that such arrangement of excitation light source reduces internal reflection from the light emitting onto a plan surface of the light source, which otherwise can be reflected back onto the array of active detection elements.

One preferred embodiment of the present invention is the use of a light source for the recording of attenuation of light, for instance through refraction and/or reflection. Often it is preferred that the light from such a light source is transmitted through the sample compartment in a substantially collimated manner, such that a substantial portion of the light is parallel or substantially parallel. It has been surprisingly found that such substantially parallel light can enhance the contrast of the attenuation, that is the ratio of attenuation of light by the biological particle to the intensity of transmitted light in a region of the background. In these and other preferred embodiments of the present invention a portion of the light transmitted through the sample is not exactly parallel, but preferably at an angle less than 45° relative to parallel, such as less than 30°, such as 15°. Even less divergence, such as 10° or less, is often preferred, such as divergence of light of no more than 5° relative to the optical axis.

It has been found that in several preferred embodiments the high contrast recorded under collimated conditions can be substantially maintained while a moderate divergence often contributes positively to evening out the intensity of light transmitted through the sample compartment and exposed onto the array of active detection elements. Often many of these embodiments have the focus point of the light source, brought about by an optical components such as lens(es) or mirror(s), substantially outside the sample compartment.

In other equally preferred embodiments of the present invention, for the recording of attenuation of light, the light from a light source passing through the sample compartment for the recording of attenuation of light is substantially focused on the sample compartment. Preferably where a substantial portion of the light transmitted through the sample compartment can be recorded by the array of active detection elements.

One feature of the present invention, which is highly preferred is that the light transmitted through, and/or onto, the sample compartment is substantially even in intensity across the field of view of the array of active detection elements. Preferably deviation from even illumination, for instance expressed as the ratio of the variation of intensity to the mean intensity, is less than 25%, more preferably less than 10% and even more preferably less than 5%. Such property generally has the effect of reducing variation in an optical property of a sample as recorded on the array of active detection elements, which often is results in lower variation in the expression of a property, which substantially is dependent on the intensity of illuminated light. This is for instance apparent for both attenuation of light and emission of fluorescence.

Optical means, consisting of number of lenses arranged in an array, can be arranged to substantially focusing multiple images of the light-emitting element of a light source onto and/or through the sample compartment. Such arrays of micro lenses are preferred in several embodiments of the present invention for the purpose of effectively illuminating a portion of the sample compartment, preferably substantially only illuminating a portion from which light is exposed onto an array of active detection elements.

One often preferred arrangement of micro lenses includes an array of cylindrical micro lenses. Such a micro lens array if preferably used in combination with a second or more array(s) of cylindrical micro lenses, which typically are oriented perpendicular to each other. Such an arrangement is included in several preferred embodiments of the present invention, mainly where it improves the efficiency of illumination by creating an even illumination across a part of the sample compartment and/or by transmitted a high fraction of the light emitted from the light source onto a part of the sample compartment. In several preferred embodiments the properties of such two or more arrays of cylindrical micro lenses are substantially identical, while in other often-preferred embodiments the properties are substantially different, such as to produce illumination which is adapted in shape to the shape of the array of active detection elements. Properties of arrays of micro lenses that are varied to produce such shape are for instance pitch of the lenses and/or the focal length.

It is often preferred to include optical means to focus light exposed onto an array of detection elements, such as one or more lens(es) or mirror(s), where such optical means have an ability to focus exposed light signals, expressed as depth of focus in the object plane. In several preferred embodiments of the present invention such focusing mean have focus depth larger than 5 μm, preferably in the range from 10 μm to 150 μm.

In order to use a single optical means for both the recording of attenuated transmitted light and emitted fluorescence light it is generally preferred that the one or more lens(es) used for focusing of light exposed onto an array of detection elements is substantially transparent to light in the wavelength regions of between 200 nm and 1,000 nm, preferably where it is transparent in the wavelength region of between 300 nm and 1,000 nm more preferably where it is transparent in the wavelength region of between 350 nm and 850 nm. Preferably the one or more lens(es) used for focusing are optically aberration corrected in the range. Preferably the transparency of the one or more lens(es) is such that attenuation of light is less than 3 OD in the region, more preferably less than 1 OD.

While emitted light such as fluorescence light are typically weak in intensity, transmitted light, such as light used to determine attenuation is often of considerable intensity. In many embodiments it is therefore often preferred to attenuate the light through the use of an optically dampening filter, preferably where the light emitted onto the sample compartment is attenuated. Preferably the dampening filter used has properties that reduce the transmitted light intensity by more than 1 OD, preferably reducing the intensity of transmitted light by as much as 3 OD.

The array of active detection elements in embodiments of the present invention is typically either a CCD or CMOS sensor.

In several preferred embodiments of the present invention, where in addition to light attenuation image, two or more florescence light intensity images are recorded, the fluorescent light is filtered using wavelength limiting means, such as filter and/or interference filters it is preferred that these filters can be interchanged between recording of images. These filters could be mounted on a fixture that is moved, such as by linear translation or by rotation.

In preferred implementation of the present invention the optical magnification of light exposed onto an array of active detection element is less than 20:1, defined as the ratio of size of projection of any dimension of an object in the sample compartment to the size of the object. Other equally preferred embodiments have optical magnification of between 1:1 and 20:1, preferably between 1:1 and 1:10. In several embodiments where large are of the sample compartment are imaged it is preferred that the optical magnification is less than 4:1, such as in the range from 1:1 to 4:1.

While several embodiments of the present invention include means with fixed optical magnification, several equally preferred embodiments include means which allow recording of images at two or more optical magnifications, which for instance can be used to facilitate detection of cells at lower magnification and subsequent detail analysis of cells at higher magnification. Some preferred embodiments include means for variable optical magnification, e.g. zoom.

As many of the preferred embodiments of the present invention include exposing a number of light intensity images for the purpose of assessing property of a biological property it is preferred that any movement of a sample or particle in a sample is kept under control, more preferably such movement should be kept at minimum. Therefore it is preferred that the volume of liquid sample is at stand still during the exposure, where stand-still is defined as the situation where at least a part of the image of a biological particle does not move any more than it is contained substantially within the boundary of the same detection elements during one exposure. Further when more than one exposer of light onto the array of detection element, for the generation of two or more images of light intensity information, it is preferred that conditions of stand-still are maintained, where stand-still is defined as the situation where at least a part of the image of a biological particle does not move any more than it is contained substantially within the boundary of the same detection elements during time of two exposures, preferably such that it is contained substantially within the boundary of the same detection elements during time of more than two exposures, such as during three, four, five or even six exposures. Most preferably conditions of stand-still are maintained during the exposure of all images of light intensity information processed for the assessment of property of biological particle.

In preferred method of the present invention the volume of liquid sample is at stand-still during the exposure, more preferably stand-still is before, during, after exposure, and therebetween. Stand-still conditions are conditions where nothing moves but such conditions can be difficult to obtain in a liquid system such as when biological particles are suspended in liquid, since there might be forces such as gravitational, or kinetical in play causing parts of the sample, including particles to move, e.g. through sedimentation or oscillation, such forces acting on the sample unintentionally, that is without active activation and/or control. It is therefore often preferred to define stand-still where conditions where no intentional force is applied to the sample, sample compartment or detection means which can cause movements. Another preferred definition is where stand-still is defined as the situation where at least a part of the image of a biological particle does not move any more than it is contained substantially within the boundary of the same detection elements during time of an exposure with a light source, such as through the time of exposure with first or a second light source, preferably where the cause of movement is unintentional.

Another equally preferred definition of stand-still is where stand-still is defined as the situation where the sample does not move relative to the array of active detection elements such that the image of a biological particle in the sample does not move any more than it is contained substantially within the boundary of the same detection elements during the gathering of light intensity information, preferably during two or more exposures, preferably where the cause of movement is unintentional. Still another equally preferred definition of stand-still is where stand-still is defined as the situation where the sample does not move relative to the array of active detection elements such that the image of a biological particle in the sample does not move any more than it is contained substantially within the boundary of the same detection elements during the gathering of light intensity information, preferably during two or more exposures, preferably where the cause of movement is unintentional.

One often preferred method to obtain stand-still conditions is to allow the sample with suspended biological particles to stand for sufficient time after movement of the sample and/or the sample compartment before initiating measurement, in order for biological particles in suspension to sediment and/or float to the inner lower and/or upper boundaries of the sample compartment, thus obtaining stand-still conditions of biological particles relative to the sample compartment. Preferably the sedimentation and/or flotation of biological particles is realised in a relatively short time, such as less than 240 seconds, preferably less than 100 seconds, such as in 45 seconds. More preferably, the settling time is longer than 10 seconds, preferably in the range between 10 and 240 seconds, more preferably in the range between 30 and 120 seconds. Stand-still may be defined as the situation where the sample does not move relative to the sample compartment. In a preferred embodiment of the present invention, the stand-still is defined as over a period of time such as of least 10 seconds, such of at least 9 seconds, such of at least 8 second, such of at least 7 seconds, such of at least 6 seconds, such of at least 5 seconds, such as at least 4 seconds, such as at least 3 seconds, such as at least 2 second, or such as least 1 second. Preferably, this period may be before, during and/or after exposure.

The volume of sample analysed usually relates to the statistical quality of the assessment of biological particles, since the size of the volume typically correlates directly to the number of individual particles that are analysed. For instance when the assessment of biological particles concerns the counting of individual particles the total number of counted particles determines the precision of the results. One parameter which has influence on the volume of sample analysed is the thickness of the sample compartment, defined by its wall parts, and therefore prefer several embodiments of the present invention that the interior of the sample compartment has an average thickness of between 20 μm and 1,000 μm. In these and other preferred implementations have average thickness is between 20 μm and 100 μm. Ideally the thickness of the sample compartment is uniform, but it has surprisingly been found that a substantial deviation from uniform thickness does not compromise the results of the assessment, as long as the average thickness of the portion of the sample compartment that is analysed is known. Further, in embodiments where the assessment of biological particles is performed in a substantially disposable sample compartment, such as sample compartments intended for only a single analysis of a sample, it is preferred that the average thickness of each sample compartment is known, or preferably determined by means of the system.

In preferred implementations of the present invention the volume of the liquid sample from which electromagnetic radiation is exposed onto the array of detection elements is in the range between 0.01 μL and 20 μL, such as between 0.05 μL and 5 μL. As the total volume of the sample being assessed, which is exposed onto the array of detection elements depends on several factors, including the sample thickness and area of the part of the sample compartment that is exposed onto the array of detection elements, it is possible to combine several features of the present invention in order to determine this volume but many of the preferred embodiments result in volume that is analysed in a single exposure that is between 0.05 μL and 1.0 μL. The total volume of the assessment can preferably be further increased by exposing additional portion of the sample, either by replacing the portion of the sample in the sample compartment with a different portion or by moving the sample compartment and thus exposing a different part of the sample compartment onto the array of sample compartment. Placement or replacement of the sample or a portion of the sample may be achieved by pumping the sample or the portion of the sample into the sample compartment with pumping means such as a pump, such as a plunger, and/or such by means of forces such as capillary forces and/or such as the gravitational force. After placement or replacement of the sample or a portion of the sample, the sample or the portion of the sample is stationary inside the sample compartment, preferably stationary due to the absence of any intentional action such as the application of a force to the sample or a portion of the sample, and that the sample compartment can be moved around so as to analyse and/or assess the sample or the portion of the sample according to the present invention.

One generally preferred embodiment, which typically has a significant contribution to the determination of the volume of sample exposed onto the array of detection elements is the view area of the optical arrangement exposing light intensity information, include embodiments where the view area are substantially fixed, or in equally preferred embodiments where the view area can be determined on the bases of the adjustment of the optical components. One preferred method for the determination of the volume analysed in a single exposure is to combine information concerning the thickness of the sample compartment with information about the active view area of the exposing system. According to an embodiment of the present invention, the thickness of the sample compartment is determined individually for the sample compartment in use. Furthermore, the sample compartment may be intended for a single analysis of a sample, and in many preferred embodiment the sample compartment can only be used for the analysis of a single sample.

Biological particles are diverse in type and properties, but it is generally preferred in several of the embodiments of the present invention that the size of the particles, the parameter or parameters of which is/are to be assessed, are of a size between 0.1 μm and 100 μm. Such size of a particle is typically the average diameter of a particle, and in several equally preferred embodiments this average size of a biological particle is between 0.1 μm and 20 μm. In other preferred embodiments of the present invention, the size is between 5 μm and 15 μm. In some embodiments of the present invention, the size is between 1 μm and 15 μm, such as at least 15 μm, at least 14 μm, at least 13 μm, at least 12 μm, at least 11 μm, at least 10 μm, at least 9 μm, at least 8 μm, at least 7 μm, at least 6 μm, at least 5 μm, at least 4 μm, at least 3 μm, at least 2 μm, or such as at least 1.

As diversity of biological particles is large as well as properties of such particles, embodiments of the present invention can be used to assess a great number of quantity and/or quality parameter of biological sample and/or particles of a biological sample. Among several of such preferred parameters are; the number of the biological particles per volume of a liquid sample, the diameter, area, circumference, asymmetry, circularity of the biological particles, determination of adhesion and/or degree of clumping of biological particles, preferably where degree of clumping allows the substantial determination of the number of individual cells in a clump of cells. Other equally preferred parameters are; the species of biological particles, the metabolic status of biological particles, intracellular property, such as number, size, shape of nucleolus.

Further one property of biological particle in a sample, often preferred where the assessment comprises the recording of two or more images of spatial light intensity information, where one image represents attenuation of light, is the substantial location of a biological particle in the spatial light intensity image. This location of a particle is preferably used to correlate other light intensity information to the particle, such as fluorescence. This is for instance often preferred when among plurality of individual particles it can be expected that some particles reflect such other light intensity information while other particles substantially do not reflect this light intensity information. The substantial absence of such light intensity information can make it difficult to determine the presence of such particle based solely on the light intensity information, as it sometimes shows no information which can be differentiated from the background. In these instances it is often preferred that the location of a particle can be derived on the bases of other image of spatial image intensities.

Preferred embodiments of the present invention include methods for the assessment of properties of biological samples and/or biological particles, where an image of spatial light attenuation information is recorded. Many of these embodiments preferably further include the steps of recording additional images of spatial light intensity information, included in the processing of image information, where the additional spatial light intensity information is information about fluorescence. In several embodiments this additional fluorescence image information is generated by excitation light from the light source passed through the wall parts of the sample compartment and used to generate attenuation image information, where an emission filter is employed thus producing fluorescence. In other equally preferred embodiments such additional fluorescence information image is generated by excitation light from an additional light source. As more information is generally recorded by recording more than one or two images of spatial light intensity information, it is generally preferred that in the addition to an image of attenuation information, two additional fluorescence information images are included in the processing of images, and typically it is more preferably to use three, four or five additional fluorescence information images. According to one embodiment of the present invention, an image of spatial light intensity information is recorded, where the spatial light intensity information is information about fluorescence, caused by excitation light from the second light source passed through the wall parts of the sample compartment. In other preferred embodiments the second spatial fluorescence light intensity information is caused by excitation light from a third light source. In another embodiment of the present invention, a third image of third spatial light intensity information is recorded, where the third spatial light intensity information is information about fluorescence, caused by excitation light from the second or third light source passed through the wall parts of the sample compartment, preferably caused by excitation light from a fourth or subsequent light source. In a third embodiment of the present invention, a fourth image of fourth spatial light intensity information is recorded, where the fourth spatial light intensity information is information about fluorescence.

In embodiments of the present invention, where parameter of a biological sample and/or biological particle include multiple images are included in the processing it is usually preferred to use two or more light sources in order to obtain the image information needed. The number and nature of the light sources, which are usually two, three, four or five individual light sources, reflects properties such as wavelength and intensity of light, attenuation and scatter, and in the case of fluorescence background suppression.

In several highly preferred embodiments of such multi-image processing it is preferred that spatial information about location of biological particles is an integrated feature of the processing of images of spatial light intensity information.

In embodiments including processing of multi-image information, parameters of biological particles that can be assessed can preferably be one or several of the following; assessment of species biological particle, condition of biological particle, preferably wherein condition of biological particle is metabolic condition such as cell cycle, viability, vitality, apoptosis, motility. In a preferred embodiment of the present invention, the location of biological particles in the first spatial light intensity image is used to determine presence of light intensity information in another recorded image of light intensity information associated to biological particles, preferably where the other light intensity information is fluorescence. In another preferred embodiment of the present invention, the location of biological particles is determined by combining information in a first and a second image of spatial light intensity information, where the images are recorded using illumination from the first light source and applying substantially different modulation means for the images, preferably where the images are dark-field and bright-field images. In yet another preferred embodiment of the present invention, the location of biological particles is determined by combining information in three or more images of spatial light intensity information, where the images are recorded using illumination from the first light source and applying substantially different modulation means for the images. The determination of intensity of a second or additional light intensity information associated to biological particles may be used for the assessment of species and/or condition of biological particle. Alternatively, the determination of intensity of a second or additional light intensity information associated to biological particles may be used for the assessment of species and/or condition of biological particle comprising a bio marker.

In many preferred embodiments of the present invention a light source used is a tuneable solid-state light source. The presence of a tuneable light source can significantly simplify the design of system according to the present invention, and would also allow for greater flexibility, such as when the tuneable solid-state light source is used for excitation of fluorescence light. Preferably such tuneable solid-state light source is either a light emitting diode (LED) or a laser diode.

EXAMPLE 1

Image Cytometer

FIG. 1 illustrates possible configuration of an Image Cytometer including several preferred embodiments of the present invention. The illustration outlines 4 main groups of components, the sample holder (100), illumination means (110), imaging means (120) and detection means (130). Finally it illustrates the main optical axis of the Image Cytometer (140), along which majority of the optical components are arranged.

The sample holder can be moved along the optical axis relative to the imaging means, in order to assure that the sample is in focus alignment with the imaging means. The sample compartment (101) is placed on the sample stage (102) in the optical path. The sample compartment is typically attached to the sample stage but it can be released there from such that it can be removed from the Image Cytometer and replaced again through either manual or automated process. The sample stage can move in two directions perpendicular to the optical axis. This allows different parts of the sample inside the sample compartment to be assessed.

The illumination means can move along the optical axis in order to maintain the desired illumination of the sample compartment. The illumination means contains usually 2 or more light sources (3 shown). The illustration shows a light source located on the optical axis (111), such that illumination of the sample in the direction towards the detector, which is often only preferred when the purpose is to generate an image of passive light attenuation and/or scattering properties, such as Bright-field or Dark-field images. In addition the illustration shows two fluorescent light sources (112), which illuminate the sample compartment at an inclination relative to the optical axis, which has been found to improve conditions under which signal from particles is identified as being different from signal from the background. It further illustrates a light source emitting a single wavelength (112a) as well as a light source emitting two wavelengths (112b), by placing two Light Emitting Diodes in a single arrangement.

The imaging means comprise collection objective (121) in an arrangement where it is possible to interchange two or more collection objectives (121a and 121b) with substantially different properties, such as nominal magnification. The two or more collection objectives are interchanged either by linear or circular movement. Light modulation means are preferably two ore more and contain a number of optically active components labelled $Y_i$ (122) and $X_i$ (123) respectively, such as filters, apertures, obstructions or phase contrast elements. The light modulation means can be moved perpendicular to the optical axis such that each of the optical components can be placed in the beam of light emitted from the collection objective, the movement can either be linear or circular. Each light modulation means preferably has a position without an optical component, such that if all light modulation means are arranged such that this empty position is located in the light beam then no modulation takes place. The imaging means contain focusing means (124) which focus the light from the collection objective onto the detector.

The detection means can be moved along the optical axis in order record a focused image of light intensity information. The information is gathered using an array of active detection elements (131), a light sensitive camera.

The operation of the Image Cytometer and collection of data is controlled by computer means (not shown). The computer means preferably is equipped with image processing means which can be used for automatic identification and assessment of biological particles.

EXAMPLE 2

Properties of Low Wavelength Microscopy

Contrast in Bright Field microscopy according to the present invention was investigated by measuring a sample of Jurkat cells (human leukemia cell line, subclone A3, ATCC CRL-2570). The measurements were performed using four light sources of different wavelength. Three of the light sources were single colour narrow-waveband Light Emitting Diodes (LEDs) and the fourth light source was a broad-waveband white LED. All light sources were in optical arrangement where emitted light was collimated when passing the sample.

The output from the narrow-waveband LEDs was used without modification but the output from the white LED was used with modification, as well as being modified using narrow-band filters. The wide-waveband light from the white LED represents typical conditions of visible microscopy. The principle wavelengths of the narrow-waveband light used in the measurement are listed in the following Table 2-1.

TABLE 2-1

List of Light Sources

| Light Source | Principal wavelength |
| --- | --- |
| LED 365 nm | 365 nm |
| LED 400 nm | 400 nm |
| LED 453 nm | 453 nm |
| White + Filter | 555 nm |
| White + Filter | 720 nm |

The sample containing the Jurkat cells in suspension was loaded into a sample compartment of about 100 µm thickness. The sample compartment was placed in the optical system and the bright field information was focused using a 2× linear magnification onto an array of active detection elements. The focus and light intensity of each of the images was adjusted to produce comparable results.

Information in the images was analysed by determining the Total Intensity Contrast of individual cells, as the ratio of integrated intensity of a cell to the intensity of the background, which is a measure of the relative attenuation of light. The results of the contrast determination are presented in the graph in FIG. 2A, which shows the observed contrast as a function of waveband of the light source. In the graph a solid line is drawn in the wavelength range from 400 nm to 750 nm which represents the observed Total Intensity Contrast when using the broad-waveband light of the white LED.

Figure 2:
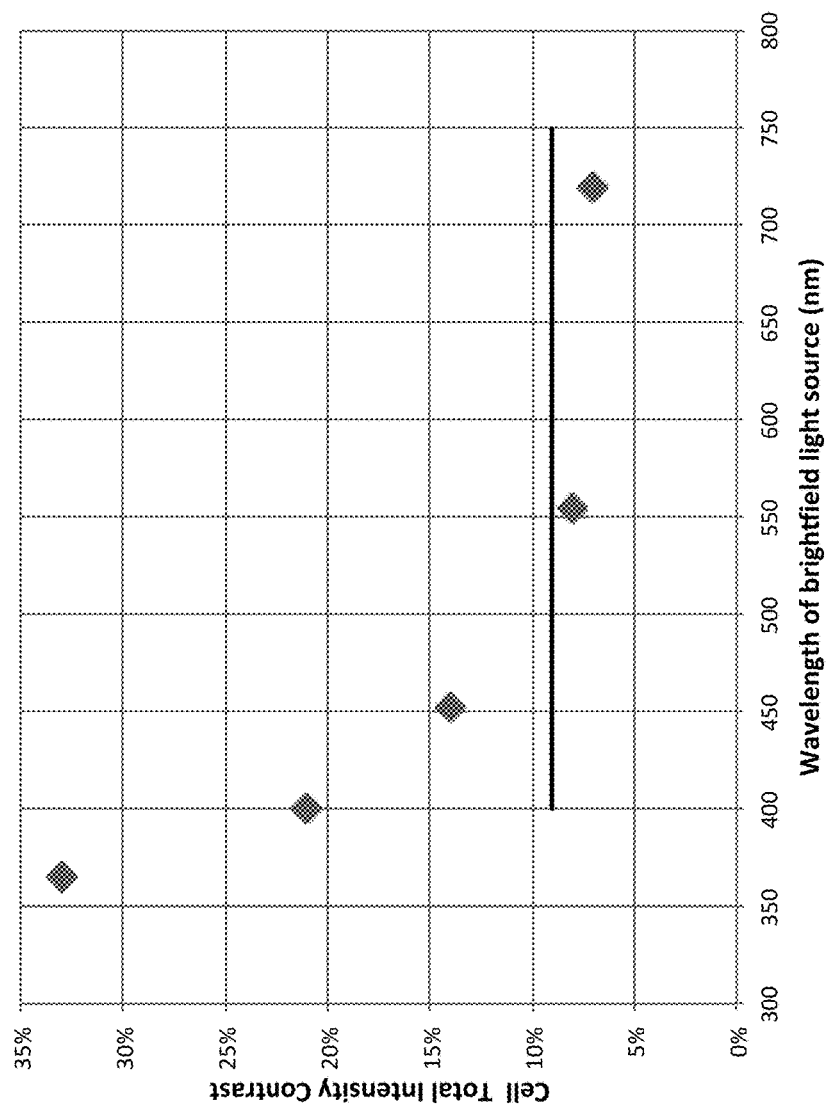
Figure 2:
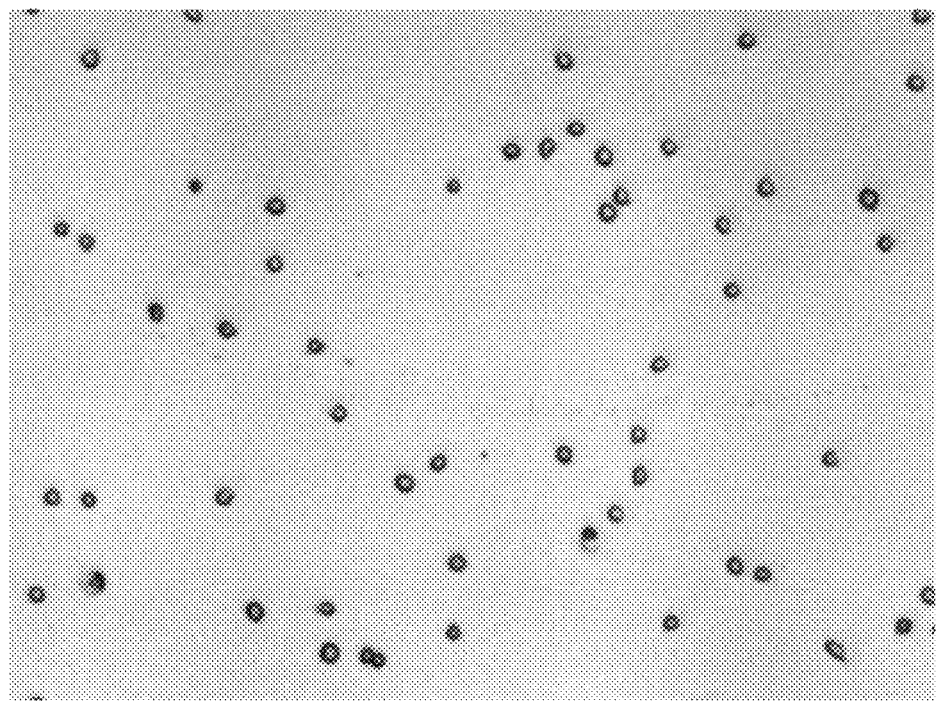
Figure 2:
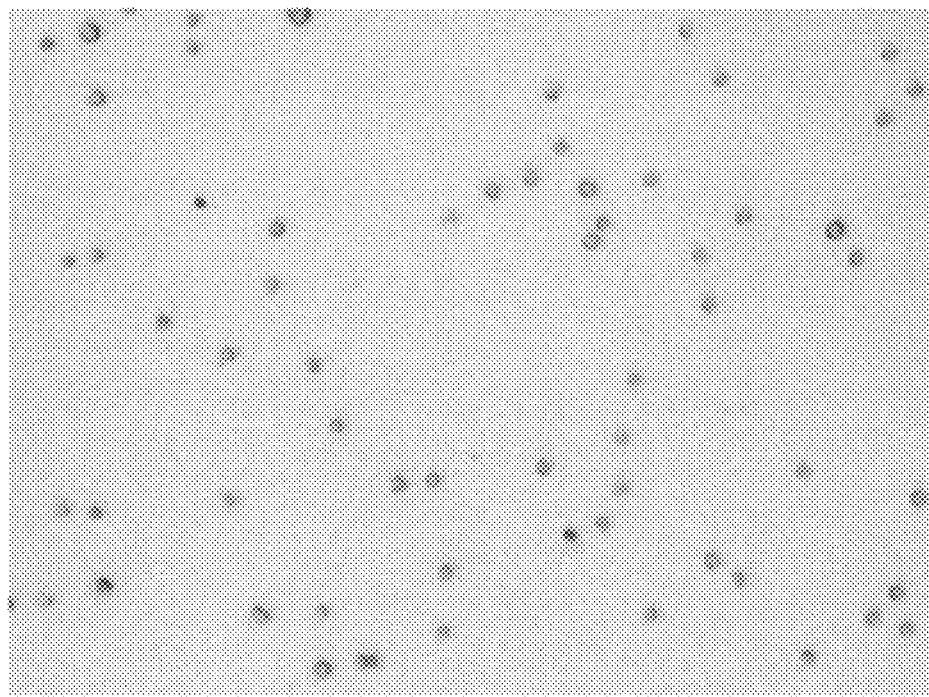
Figure 2:
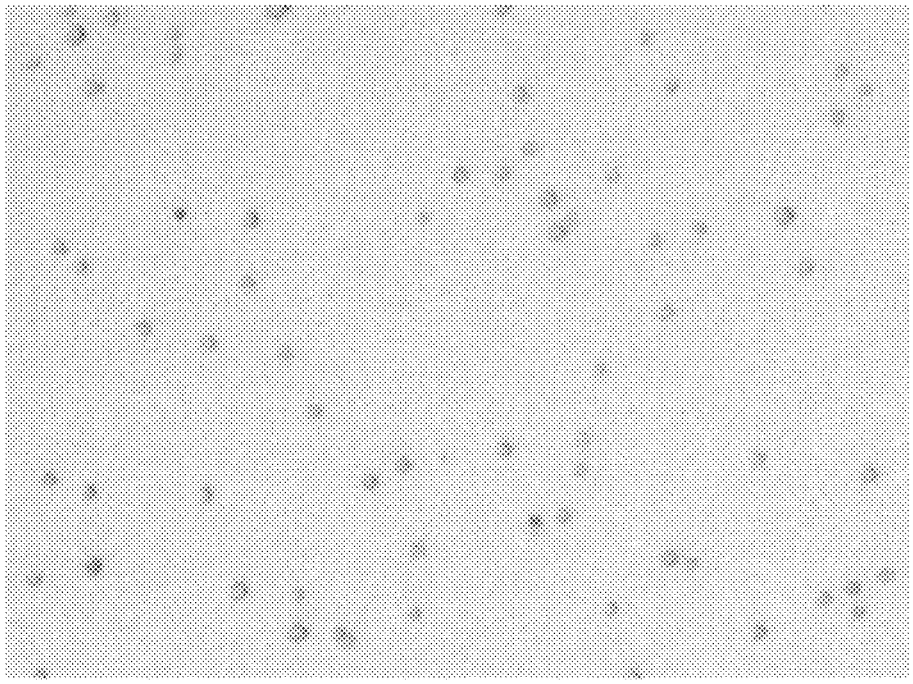
Figure 2:
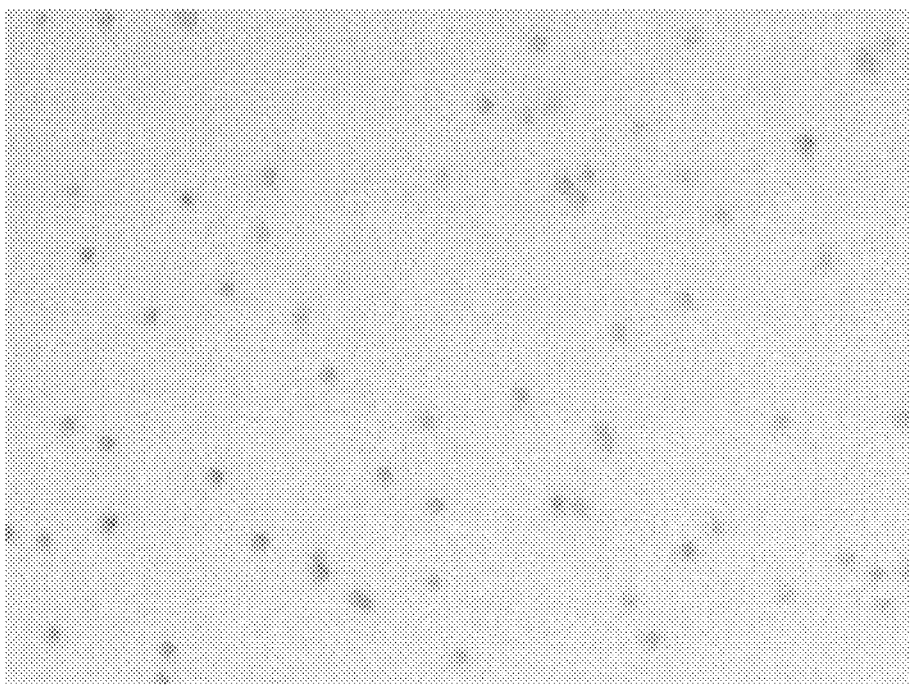
Figure 2:
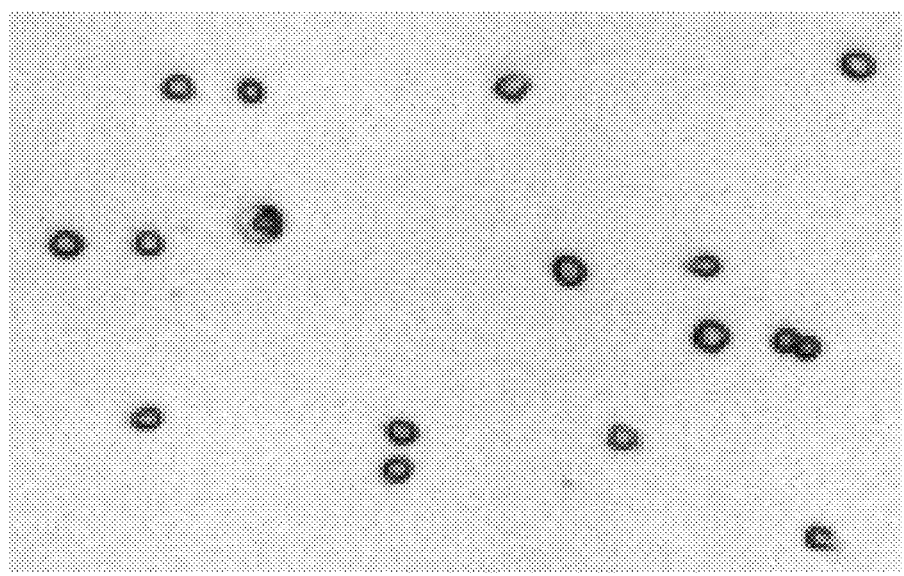
Figure 2:
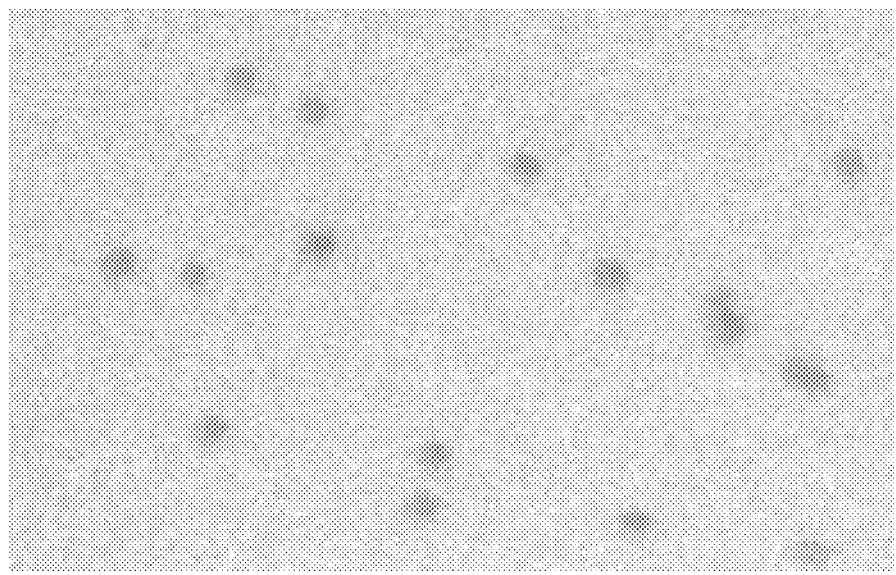

FIGS. 2B through 2G show examples of the recorded images. FIG. 2B is image recorded using light of 365 nm, 2C using light of 400 nm, 2D using white light and FIG. 2E using light of 710 nm. The images show that the contrast in the images has profound influence on the image representation of the biological particles for the purpose of accurate identification of the presences and spatial position of the cells.

FIGS. 2F and 2G show sections of the collected images in higher resolution. In FIG. 2F it is the image using 365 nm light and in FIG. 2G it is the image using 710 nm light. The images show that using light at wavelength below 400 nm results in an image that shows more details than image collected using long-wavelength light, although images are collected under similar conditions. Image of 365 nm light shows fair amount of details about shape, size and relative position than does the long-wavelength image.

EXAMPLE 3

Enhancement of Signal to Background

When performing fluorescence analysis of a biological sample it is important to manage excitation and emission light in order to obtain adequate contrast in the image. There are basically two approaches to improving contrast, firstly to use an excitation filter to reduce light of wavelength longer than what is used for the excitation of fluorescence and secondly to use an emission filter to reduce light of wavelength shorter than the fluorescent light from reaching the array of active detection elements.

In order to perform high-sensitivity fluorescence analysis, where signal contrast is an important aspect, it is necessary to consider all aspects of the optical system which affect the collected intensity information. This includes aspects such as excitation intensity, auto-fluorescence of any component of the system and attenuation of optical filters. In the task of improving contrast in collecting fluorescence spatial intensity information of a biological sample it is of importance to firstly optimise the intensity of fluorescence signal and secondly to minimise background signal. The intensity of fluorescence signal is mainly determined by the intensity of excitation light. The intensity of background signal is dependent on several aspects such as exposure of excitation light onto the array of active detection elements and intensity of auto-fluorescence of optical components.

Ideally exposure of excitation light onto the array of active detection elements can be eliminated by the use of an emission filter with infinite attenuation or blocking. Such ideal filters are difficult to realise and filters generally attenuate light to a fraction at a given wavelength, such as $10^{-6}$ to $10^{-7}$ (attenuation of between six and seven order of magnitude), and therefore in addition to high quality filters it is necessary to consider other aspects which affect exposure of excitation light. The orientation of the excitation light source relative to the field of view of the array of active detection elements can have great influence on the exposure of excitation light onto the detection elements, where general orientation directly along the axis of field of view of the detection elements will normally give rise to highest intensity of exposed excitation light. General orientation of excitation light off the field of view axis will reduce the intensity of exposed excitation light onto the detection elements.

Figure 3:
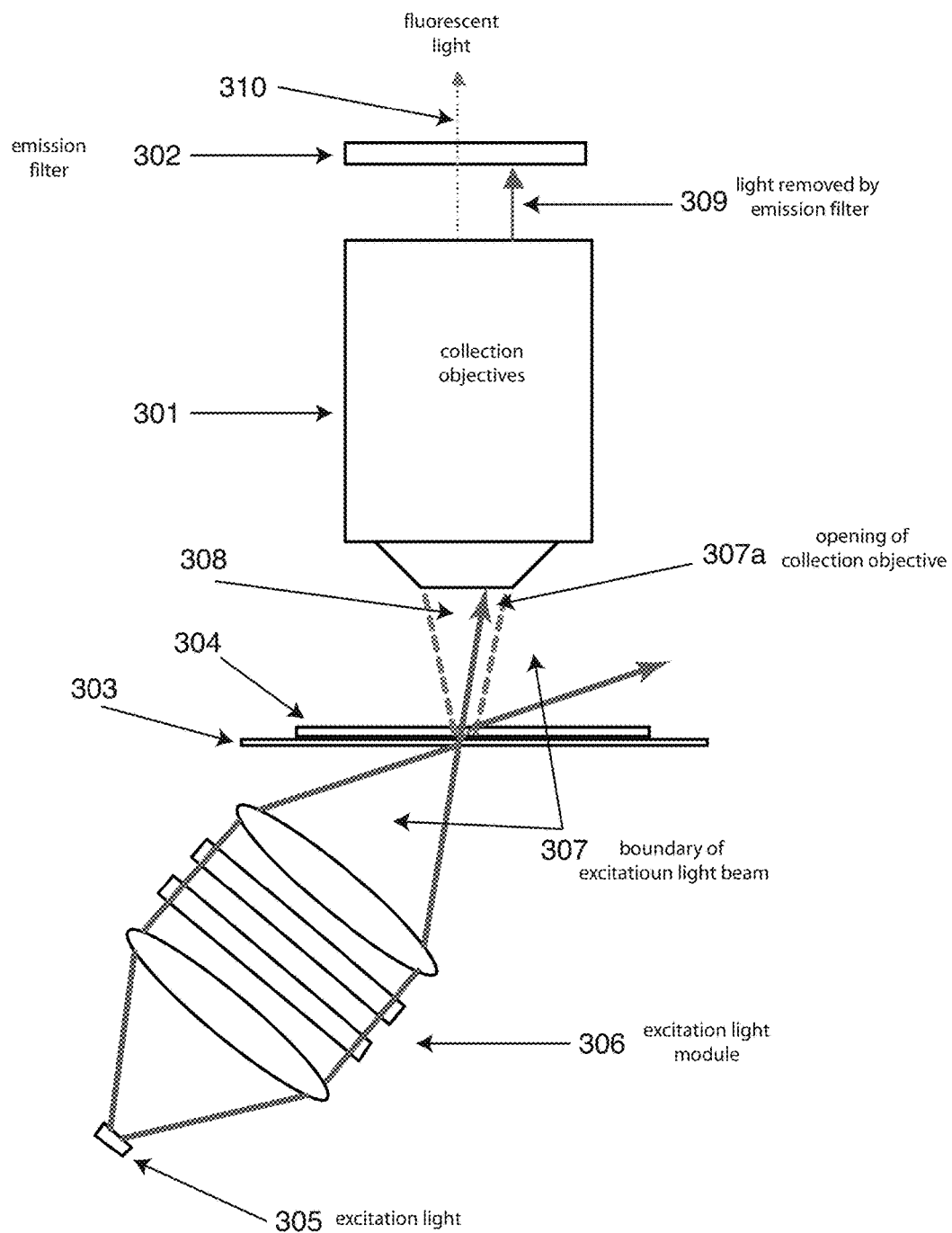
FIGS. 3A, 3B, 3C, 3D, 3E, and 3F illustrate arrangements of inclined light sources and effect of masking of the light.
Figure 3:
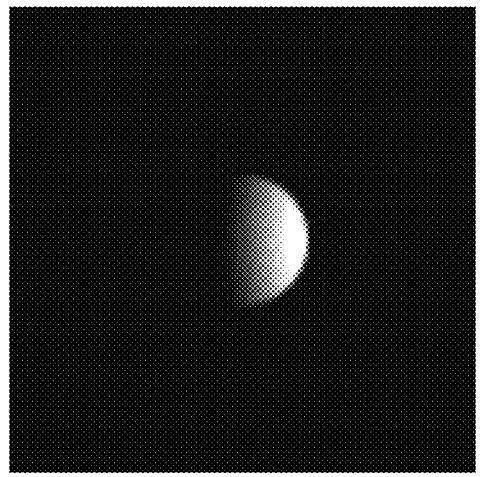
Figure 3:
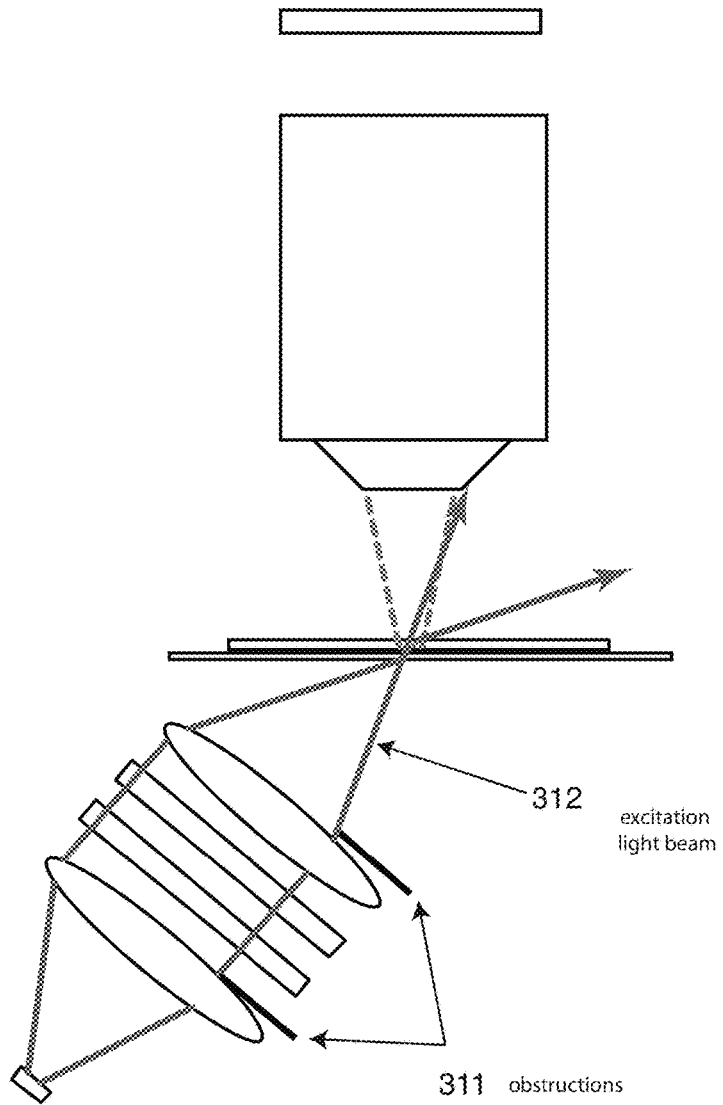
Figure 3:
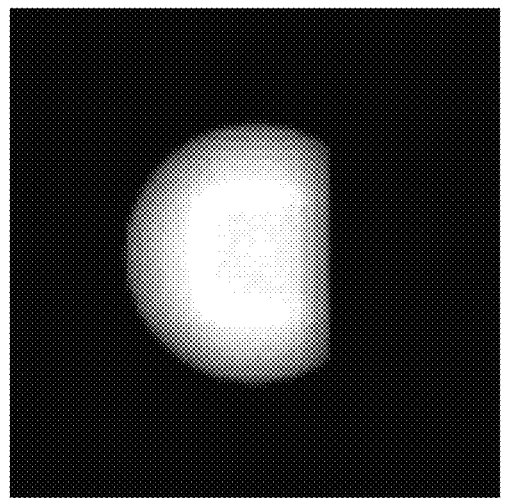
Figure 3:
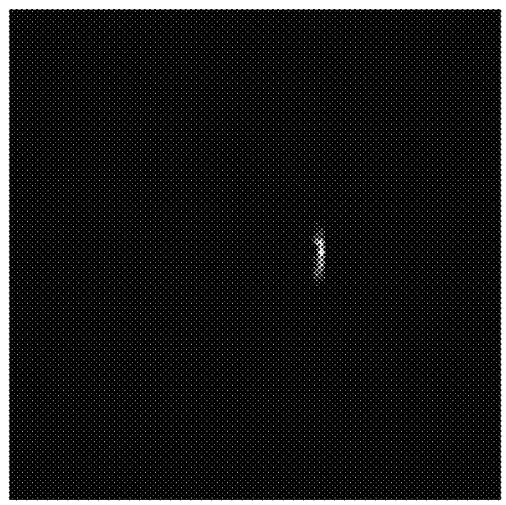
Figure 3:
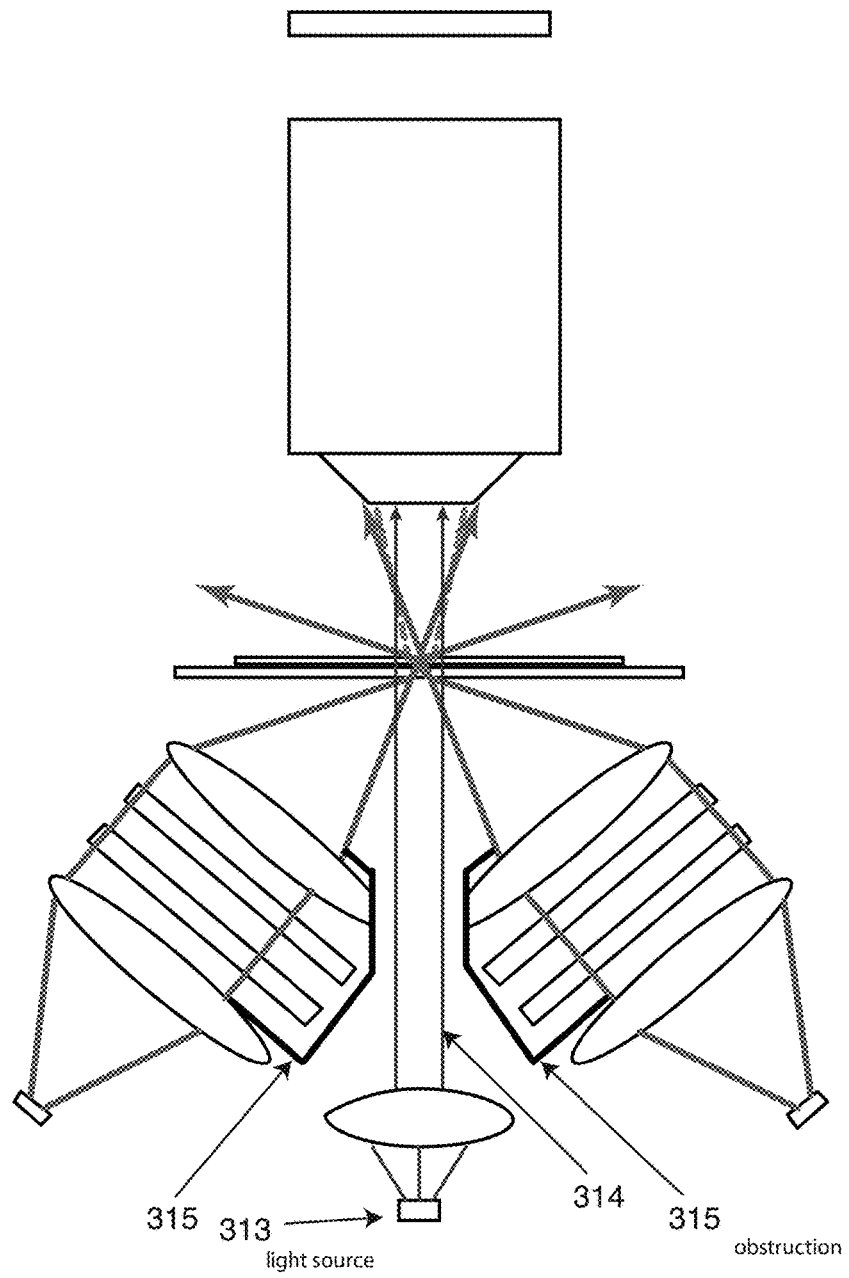

In a preferred embodiment of the present invention the excitation light is directed towards the sample in the sample compartment at an angle to the axis between the sample compartment and the array of active detection elements. Such an embodiment is shown in FIG. 3A where the general axis of the excitation light is at about 40 degrees to the axis between the sample compartment and the array of active detection elements. In FIG. 3A shows a collection objective (301) which collects light from the sample compartment, defined by a transparent wall part (303) defining the bottom of the sample compartment and another transparent wall part (304) defining the top of the sample compartment. The objective transmits the light from the sample compartment through an emission filter (302) and images it onto the array of active detection elements (not shown).

The excitation light is produced by a Light Emitting Diode (305), the light from which is collected by the first lens in the excitation light module (306), which consists of one or more lenses (two shown) and one or more light modulation elements (two shown), such as excitation filter and light dispersive element. The light from the excitation light module is focused onto the sample compartment as indicated by the boundary of the light beam of the excitation light (307). Under conditions such as those given in the figure, it is possible that a part of the excitation light can enter the field of view of the collection objective, either by scattering (not shown) or by direct illumination which can occur if a part of the excitation light beam enters the opening of the collection objective (307a) at angles below the acceptance angle. A great fraction of this light is removed by the emission filter before it reaches the detection elements (309) while fluorescent light is allowed to reach (310). Although the emission filter has great attenuation it is limited, for instance to a factor of $10^{-7}$, which means that this fraction of the light, although small, can reach the detection elements. Further the elements of the collection objective can produce fluorescence (auto-fluorescence) which will pass the emission filter and produce a background image on the detection elements.

FIG. 3B gives an illustration of the light intensity at the entry of the collection objective corresponding to the fraction of the beam of excitation light (307a). From the arrangement of the components of the excitation module it would be possible to reduce this light by limiting the aperture of the excitation light module but this would greatly reduce the total amount of excitation light exposed onto the sample compartment and thus similarly reduce the fluorescence intensity. A preferred embodiment of the present invention is illustrated in FIG. 3C, where an obstruction(s) (311) is/are placed in the excitation light module, thus changing the light beam of the excitation light (312) which largely removes the rays of light which would enter the field of view of the collection objective.

FIG. 3D shows the intensity profile of the modified light beam of excitation light, where a fraction is removed by the obstruction. FIG. 3E show the resulting light intensity entering the collection objective, and comparison to FIG. 3B it shows that the extension of light has been greatly removed but further in this example it is important to note that the scaling of the two images is such that FIG. 3E has been amplified by a factor of approximately ×200, illustrating that the intensity of the excitation light has been reduced effectively.

In a preferred embodiment of the present invention the excitation light is directed towards the sample in the sample compartment at an angle to the axis between the sample compartment and the array of active detection elements. Such an embodiment is shown in FIG. 3F which shows the same configuration of the excitation light source and optical elements as in FIG. 3A. The configuration in FIG. 3F further shows a cover (315), e.g. in the form of an aperture, for reducing the amount of excitation light reaching the objective. The embodiment in FIG. 3F further shows a light source (313) located on the optical axis extending from the array of active detection elements to the sample compartment. This configuration is similar to the one shown in FIG. 5A. The light from the light source in FIG. 3F was passed through optical means such that it formed a beam of light (314) that was substantially parallel to the optical axis of the collection objective such that the beam of light is collimated.

The following Table 3-1 shows the effect of the size of the obstruction on the intensity of the excitation illumination and the intensity of excitation light entering the collection objective. The table shows the relative amount of excitation light exposed onto the sample compartment as well as the relative amount of the light beam of excitation light that enters the collection objective. The obstruction is formed by placing a linear screen into the cylindrical beam of light inside the excitation light module and the reported values are the insertion of the obstruction relative to the diameter of the light beam.

TABLE 3-1

Excitation Light and Light in Collection Objective

| Obstruction | Excitation Light | Light in Objective |
|---|---|---|
| 0% | 100% | 11% |
| 6% | 98% | 8% |
| 13% | 93% | 3% |
| 19% | 85% | 0.8% |
| 22% | 81% | 0.18% |
| 25% | 77% | 0.005% |

The effect in the analysis of weakly fluorescent particles, for instance particles containing relatively few fluorochromes, is demonstrated in the following using typical conditions. In an embodiment of the present invention let us assume the use of a collection objective with Numerical Aperture (NA) of 0.20. Further let us assume that fluorescence conversion efficiency of the particles is $2\times10^{-6}$ and similarly that the fluorescence conversion efficiency of the sample compartment is $2\times10^{-7}$, this fluorescence originating from impurities in the transparent wall part and/or other materials. The emission filter attenuates majority of the excitation light entering the collection objective but upon entering the collection objective the light can give rise to substantial background fluorescence, caused by impurities in optical components as well as other materials in the collection objective, and substantial part of this fluorescence will pass through the emission filter. Therefore there is a net light intensity transmitted through the emission filter onto the detection elements, caused by excitation light entering the collection objective, and we can assume that the net intensity of scattered, exposed and fluorescent light passing the emission filter amounts to $5 \times 10^{-7}$.

These conditions describe a system where it is very difficult to assess fluorescence intensity from a biological particle, since the total intensity of the background is approximately 3 times that of the fluorescence intensity observed from the particle. By inserting an obstruction the beam of excitation light in the excitation light module it is possible to reduce the amount of light entering the collection objective and thus suppress the background signal significantly. In Table 3-1 we have shown that at the same time the total amount of excitation light entering the sample compartment is also reduced to a much less extent. The effect of this illustrated in the following Table 3-2, which shows normalised fluorescence and background signals.

TABLE 3-2

Normalised Fluorescence and Background Signals

| Ob-struction | Fluo-rescence | Sample Back-ground | Light in Objective | Back-ground | Signal/Back-ground |
|---|---|---|---|---|---|
| 0% | 1.00 | 0.10 | 2.67 | 2.77 | 0.36 (1) |
| 6% | 0.98 | 0.10 | 1.98 | 2.08 | 0.47 (1.3) |
| 13% | 0.93 | 0.09 | 0.74 | 0.83 | 1.1 (3.1) |
| 19% | 0.85 | 0.09 | 0.16 | 0.24 | 3.5 (10) |
| 22% | 0.81 | 0.08 | 0.04 | 0.12 | 6.8 (19) |
| 25% | 0.77 | 0.08 | 0.00 | 0.08 | 9.6 (27) |

Table 3-2 shows that the total background signal reduces significantly more rapidly than the fluorescence intensity, which is illustrated in the Signal/Background (S/B) values (in parenthesis is the relative change in the ratio of fluorescence signal to background signal). The results of Table 3-2 suggest that under these conditions the S/B ratio increases almost 30 fold by placing an obstruction in the beam of excitation light than covers about 25% of the diameter of the light beam. Under these conditions the intensity of fluorescent light has declined by only 23%.

EXAMPLE 4

Detection of Particle Standard

A system according to the present invention was used to identify and quantify calibration beads, which typically are used to calibrate flow cytometry instruments. The beads were Rainbow Calibration Particles (P/N RCP-30-5A), Spherotech USA a set of beads 3 μm in diameter comprising 8 groups producing different intensities of fluorescence.

The image cytometer of the present invention was set to illuminate the sample with excitation light in a narrow band around 475 nm and to detect fluorescence emission in a waveband at around 536 nm. Light from the sample compartment was collected using 4× collection objective with NA 0.20 and focused onto the array of active detection elements. The beads were handled according to instructions provided by the supplier and placed in a sample compartment of approximately 100 μm thickness.

Series of images of spatial light intensity information were collected by an array of active detection elements, firstly an exposure of spatial bright field light intensity information was collected for the purpose of acquiring information concerning the position of the particles and secondly an exposure of spatial fluorescence light intensity was collected using integration time of 300 ms. A total of 35 pairs of bright field and fluorescence images was collected from different parts of the sample by moving the sample compartment, resulting in a total of 70 light intensity images.

Figure 4:
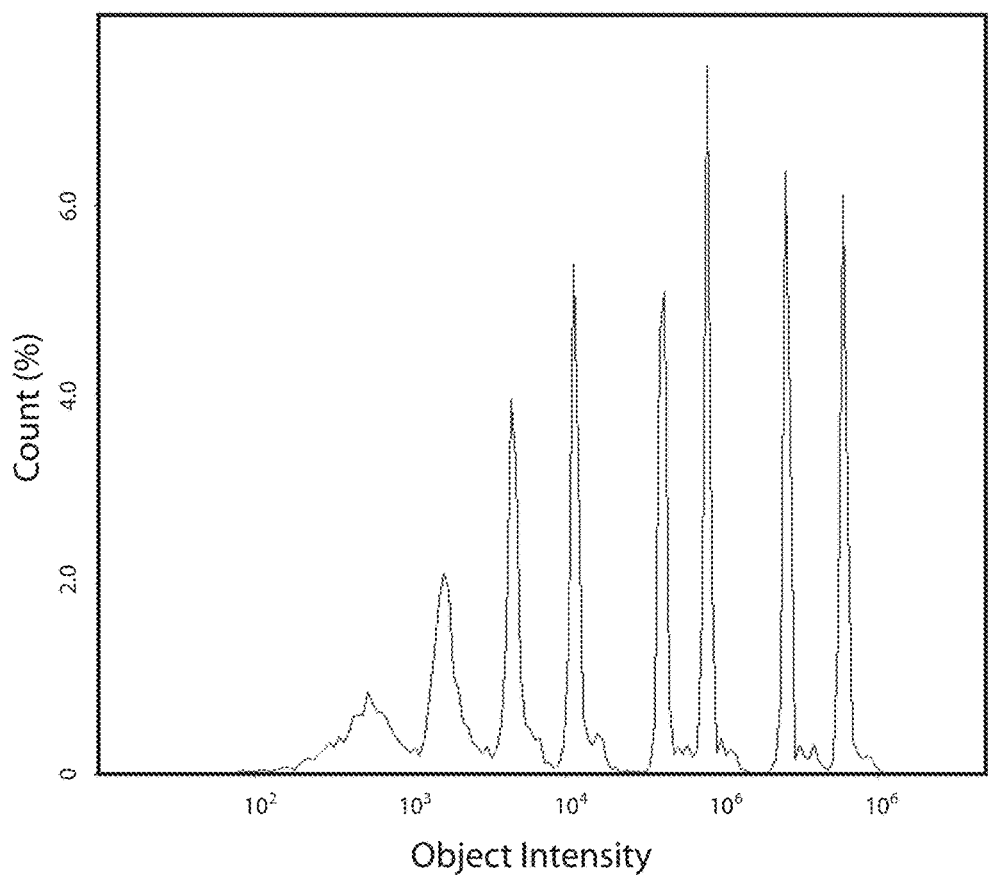
FIG. 4 shows a graph that illustrates intensity of fluorescent polymer beads.

Each bright field image was used to determine the position of a particle and this information was used to interrogate the fluorescence image at that location, integrating the total intensity of fluorescent light from each particle. A total of 12,750 particles were analysed and the results are presented in FIG. 4, which shows a histogram of observed fluorescent intensities. The figure shows clear distinction of 8 different intensity groups, in compliance with the specifications given by the suppliers of the calibration beads. This demonstrates that sensitivity of an image cytometer according to the present invention is similar to a typical flow cytometer of the day.

EXAMPLE 5

Bright-Field/Dark-Field Configuration

Figure 5:
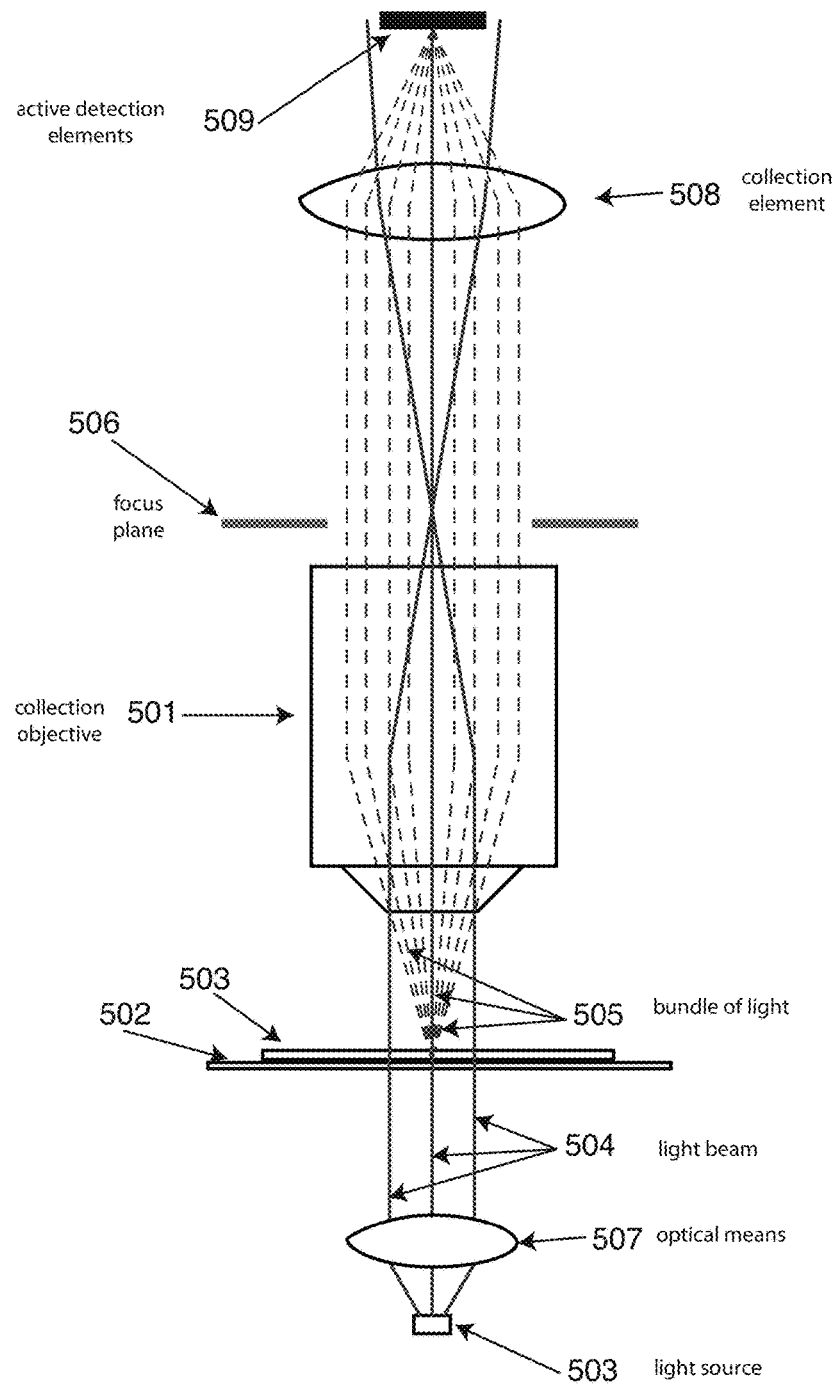
FIGS. 5A, 5B, 5C, 5D, 5E, 5F, 5G, 5H, 5I, 5J, and 5K illustrate configuration of passive light modulation in Bright-field images.
Figure 5:
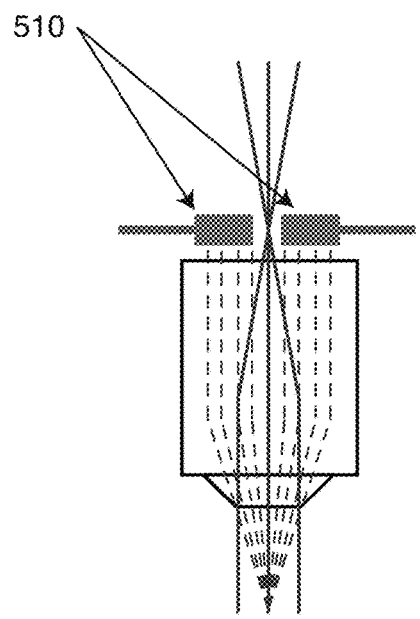
Figure 5:
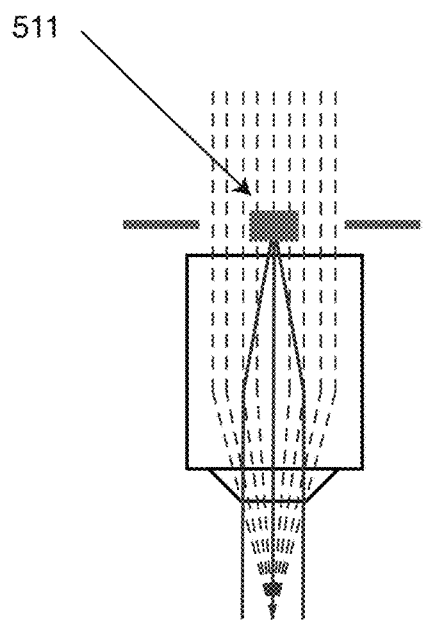
Figure 5:
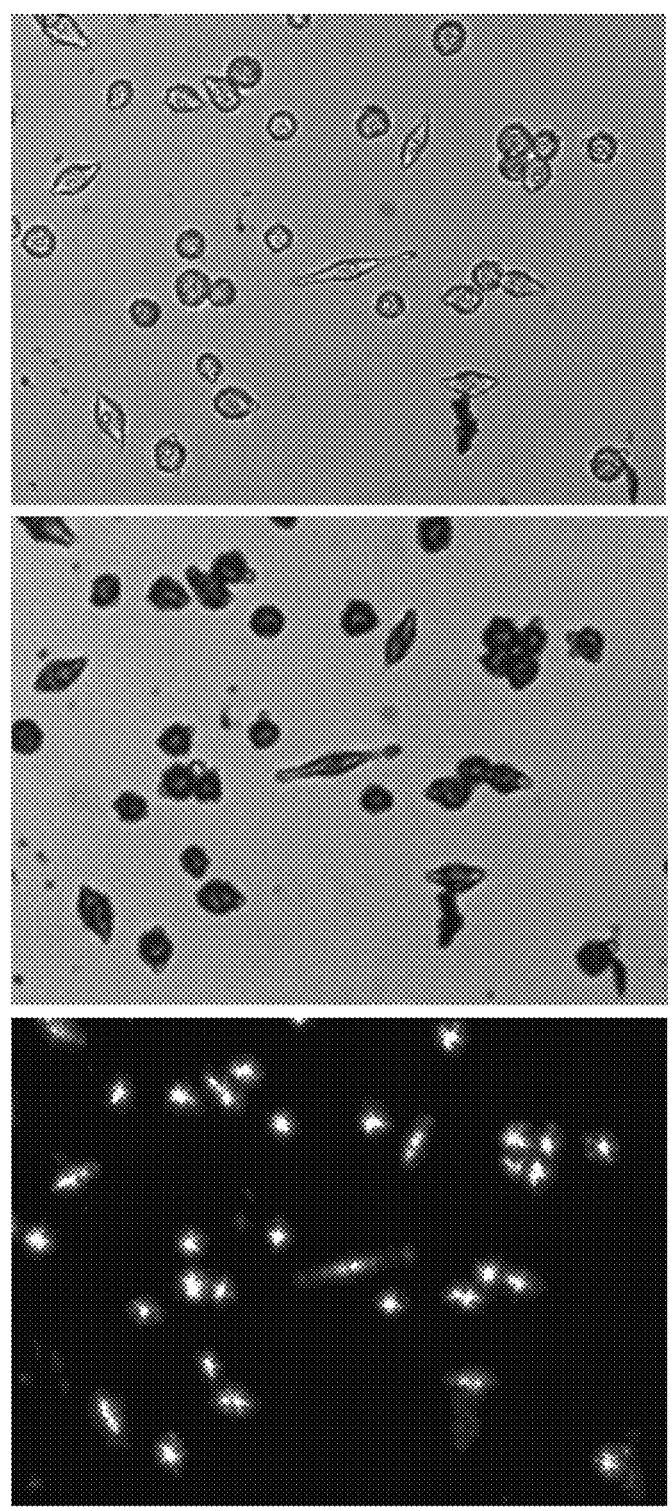
Figure 5:
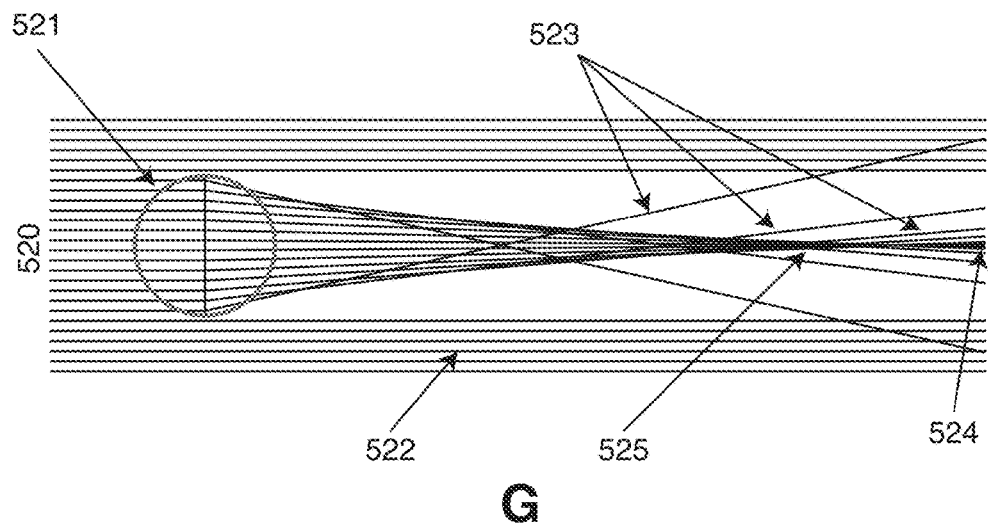
Figure 5:
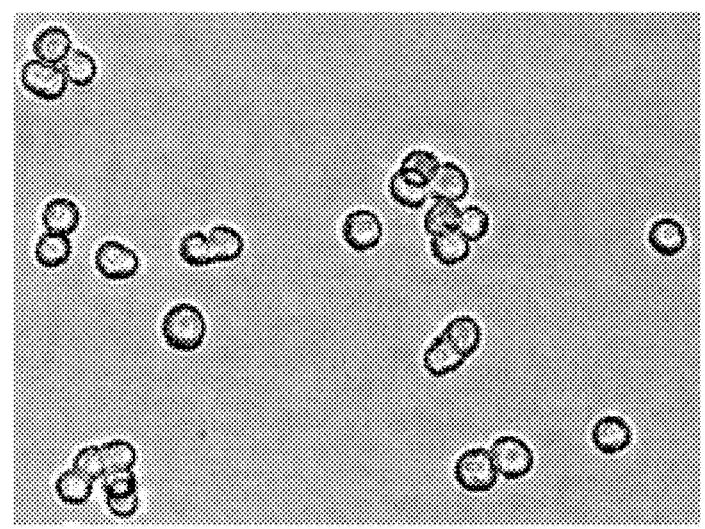
Figure 5:
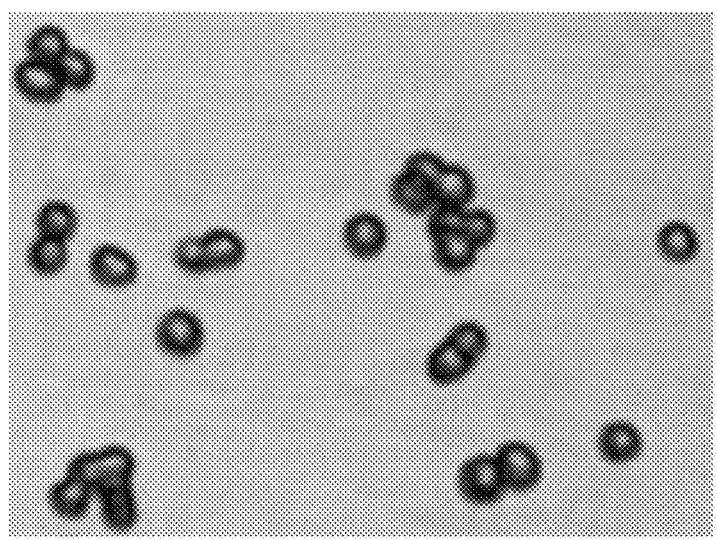
Figure 5:
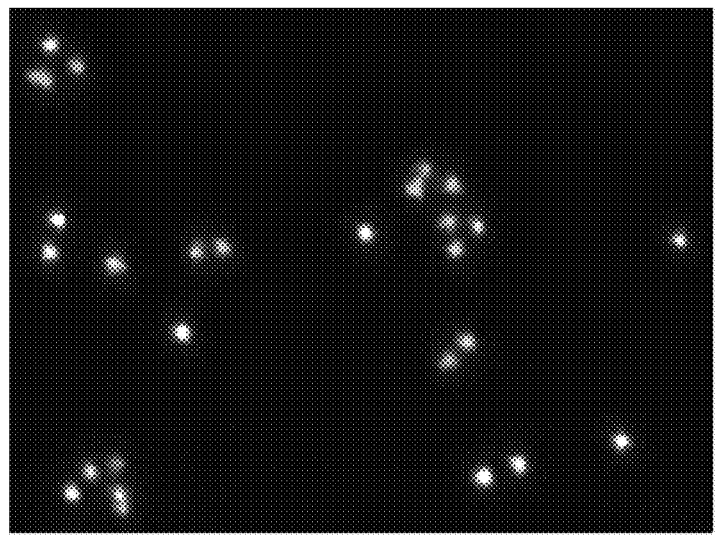
Figure 5:
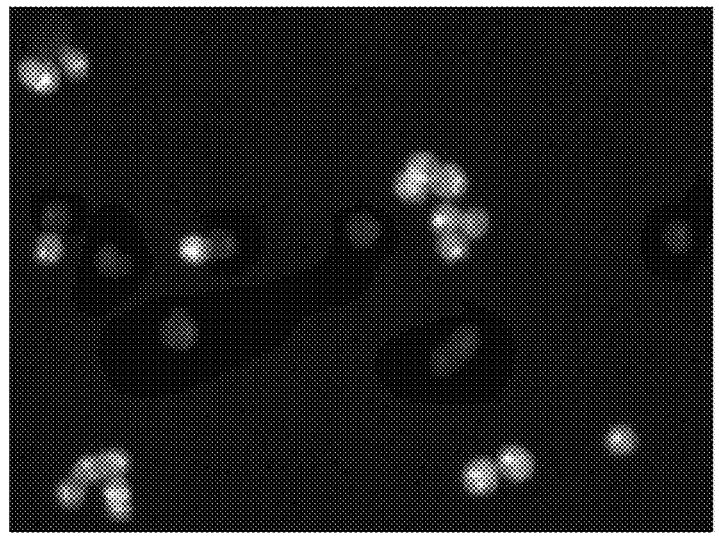

A sample of adherent WeHi-S cells (murine fibrosarcoma cell line) was placed in an image cytometer of the present invention depicted schematically in FIG. 5A and illuminated with light source (503) emitting light in a narrow waveband around 365 nm. The light source was located on the optical axis extending from the array of active detection elements (509) to the sample compartment defined by two transparent wall parts (502 and 503) exposing light towards the detection elements.

The exposed light was passed through optical means (507) such that it formed a beam of light (504) that was substantially parallel to the optical axis of the collection objective (501). The properties of the collection objective used is such that the parallel light emitted from the light source is substantially focused onto a plane (506) located along the optical axis between the objective and the array of active detection elements such that a substantial part of that light is directed away by the collection element (508) that focuses light onto the detection elements. Using this arrangement a portion of the light emitted from the light and passed through the collection objective enters the detection elements forming uniform background intensity, unless if that light is deflected by a particle in the sample then light from that location of the sample attenuates the light intensity thus forming a spatial bright field image of the particle.

The light that is deflected by the particle is affected by the elements of the particle. The light such deflected changes direction and it is emitted in several directions, the intensity of the light in different directions being determined by the properties of the particle. Some of the deflected light enters the collection objective and forms a bundle of light (505) of different directions originating from the particle. The deflected light entering the collection objective forms a substantially parallel beam of light when it reaches the collection element, which will be focused onto the collection elements. This deflected light forms a spatial image of light intensity information that is mixed with the bright field image of the sample, an example of which is given in FIG. 5D.

FIG. 5B shows an obstruction (510) that is placed in the focal plane of the substantially parallel light emitted from the light source, located between the collection objective and the detection elements. This obstruction is an aperture formed by a hole in a disk, the dimension of the hole being such that it substantially only allows light from the light source to reach the detection elements eliminating light dispersed by the particles. The resulting image, an example of which is given in FIG. 5E, is a spatial image of bright field light information, where contrast is substantially improved compared to an arrangement without said aperture obstruction discussed previously. An additional property of this arrangement is that such bright field image is considerably less sensitive to focusing of the collection objective, since focusing of this bright field image is largely dependent on the degree of collimation of the light passing through the sample compartment and the dimension of the aperture of the obstruction, thus facilitating images with substantially large focus depth.

FIG. 5C shows an obstruction (511) that is placed in the focal plane of the substantially parallel light emitted from the light source, located between the collection objective and the detection elements. This obstruction has dimensions and is located such that it substantially only allows light dispersed by the particles to reach the detection elements eliminating light emitted directly from the light source. The resulting image, an example of which is given in FIG. 5F, is a spatial image of dark field light information of the particles in the sample.

FIG. 5G illustrates rays of light interacting with a spherical object which properties, with regard to refractive index, are similar to those of a biological particle. It shows that when collimated light (520) illuminates the particle (521) that the rays of light are refraction due to difference in refractive index, the degree of refraction being determined by the optical properties of the particle. The light passing around the particle (522) enters the collection objective (not shown) still collimated. Some of the light is dispersed at large angles (523), such that they will illuminate the plane of the entrance of the collection objective outside the entrance, thus not reaching the array of detection elements (not shows). Other rays are refracted at small angles (524), such that they will enter the collection objective and thus being, imaged on the detection elements.

Considering the collimated rays of light which pass around the particle, these will form an image on the detection elements with considerable light intensity outside the image of the particle and small or no light intensity inside the particle, thus forming a shadow of the particle. The rays of light interacting with the particle are refracted to a different degree, some of which have zero angle of refraction, since they cross the boundary of the particle at perpendicular, while others have varying angle of dispersion. Considering dispersed rays of light these will form an image of the particle, to some extend similar to an image which would be observed if the particle were luminous, but with a different point of dark-field focus (525) not coinciding with the position of the particle, the point of focus being determined by the size and optical properties of the particle.

FIG. 5H through FIG. 5J show images of CHO cells in suspension recorded using different illumination condition. FIG. 5H is a bright-field image of the cells, while FIG. 5I is a bright-field image where refracted light has been blocked by placing an aperture at the focus plane of parallel light (see FIG. 5B) and FIG. 5J is a dark-field image where collimated light has been blocked (see FIG. 5C), all images are focused individually. Finally FIG. 5K is a fluorescence image of the particles showing specific staining. The images in FIGS. 5H, 5I and 5J are used in combination to determine location and outlines of individual cells, information that is used to count the number of cells and to estimate fluorescence intensity of individual cells, which is used to classify cell property.

By arrangement where the obstruction(s) in the focal plane of the collection objective are interchangeable it is possible to realise an image cytometer system that has the flexibility of recording high contrast bright field or dark field, or the combination of the two, simply by placing or removing a suitable obstruction.

We claim:

1. An image cytometer, comprising:
    a first light source configured for emitting light with a wavelength less than 400 nm into a sample region;
    a collimator for forming collimated light from the first light source and directing the collimated light along an optical axis of the cytometer and into the sample region;
    a second light source comprising a first excitation light source configured for emitting excitation light into the sample region;
    image forming means for forming at east one image of at east part of the sample region on an array of detection elements;
    the sample region located between the collimator and the array of detection elements, the sample, region adjacent to the collimator such that the light that passes the sample region is collimated light;
    wherein the image cytometer is operable in a bright-field mode, the bright-field mode being provided by having the light with a wavelength less than 400 nm into the sample region, the collimator adjacent to the sample region such that the light that passes the sample region is collimated light, so as to form the at least one image being a bright-field image.

2. The image cytometer according to claim 1, wherein the image cytometer is operable in a dark-field mode, the dark-field mode being provided by having the light with a wavelength less than 400 nm, the collimator directly adjacent to the sample region such that the sample region is in the path of the collimated light, so as to form the at least one image being a dark-field image.

3. The image cytometer according to claim 1, wherein the image cytometer is operable in a fluorescence mode, the fluorescence mode being provided by having the excitation light, so as to form the at least one image being a fluorescence image.

4. The image cytometer according claim 3, wherein the excitation light is at an incidence angle relative to the optical axis so as to provide the fluorescence image.

5. The image cytometer according to claim 1, wherein:
    the at least one image being formed in the presence of the light with a wavelength less than 400 nm further includes a dark-field image;
    the at least one image being formed in presence of the excitation light is a fluorescence image; and
    the image cytometer is configured to be interchanged between forming the bright-field image, the dark-field image and the fluorescence image.

6. The image cytometer according to claim 5, where interchanging between forming the bright-field image and the dark-field image is realised by modulation means located between the sample region and the array of detection elements.

7. The image cytometer according to claim 6, wherein the modulation means comprises an aperture configured for attenuating light during the formation of the bright-field image, wherein the light is passing the sample region as collimated light.

8. The image cytometer according to claim 6, wherein the modulation means comprises an obstruction configured for attenuating light during the formation of the dark-field image, wherein the light is passing the sample region as non-collimated light.

9. The image cytometer according to claim 6, wherein the modulation means comprises phase contrast microscopy modulation means.

10. The image cytometer according to claim 1, wherein the wavelength from the first light source is between 300 nm and 395 nm.

11. The image cytometer according to claim 1, wherein the light source(s) is/are configured for emitting light in duration between 0.0001 and 0.1000 second.

12. The image cytometer according to claim 1, wherein the light source(s) is/are configured for emitting light in duration for more than a 1 second.

13. The image cytometer according to claim 1, wherein the light source(s) is/are optically connected to optical means configured for providing light with a uniform intensity across the sample region and/or across a region imaged by the array of detection elements.

14. The image cytometer according to claim 13, wherein the optical means comprises an array of micro lenses.

15. The image cytometer according to claim 13, wherein the optical means comprise two arrays of cylindrical micro lenses, wherein the lenses in one of the arrays are orientated with a major axis being perpendicular to a major axis of the lenses of the other array.

16. The image cytometer according to claim 1, wherein the image forming means is configured for transmitting light in the wavelength region of between 200 nm and 1000 nm.

17. The image cytometer according to claim 1, wherein the sample region is adopted to hold a liquid sample with biological particles.

18. The image cytometer according to claim 1, wherein the sample region is in a sample compartment being configured to transmit wavelength less than 400 nm.

19. A method for the assessment of at least one quantity parameter and/or one quality parameter of a biological sample, comprising:
   applying a volume of the biological sample to a sample compartment having parallel wall parts defining an exposing area, the wall parts allowing light from an image cytometer to pass through the wall parts of the sample compartment, wherein the image cytometer comprises a first light source configured for emitting light with a wavelength less than 400 nm into the sample compartment, a collimator for fainting collimated light from the first light source and directing the collimated light along an optical axis of the image cytometer and into the sample compartment, and a second light source comprising a first excitation light source configured for emitting excitation light into the sample compartment, the image cytometer further comprising image forming means for forming at least one image of at least part of the sample compartment on a 2-dimensional array of active detection elements;
   illuminating the sample compartment with the collimated light from the first light source, and exposing, onto the 2-dimensional array of active detection elements, light having passed through the sample compartment, thus recording an image of spatial light intensity information;
   illuminating the sample compartment with excitation light from the first excitation light source, and exposing, onto the 2-dimensional array of active detection elements, fluorescent light having passed through the sample compartment, thus recording a fluorescent image of spatial light intensity information;
   processing both images in such a manner that light intensity information from individual biological objects are identified as distinct from light intensity information from the background; and
   correlating the results of the processing to the at least one quantity parameter an or quality parameter of biological particles in the biological sample,
   the sample compartment located between t e collimator and the array detection elements, the sample compartment adjacent to the collimator such that the light that passes the sample compartment is collimated light,
   wherein the image cytometer operable in a bright-fieled mode, the bright-field mode being provided by having the light with a wavelength less than 400 nm into the sample region, the collimator adjacent to the sample region such that the light passes the sample region is collimated light so, as to form the at least one image being a bright-field image.

20. The method according to claim 19, wherein two or more images of spatial light intensity information, recorded using the first light source, are used in the processing of light intensity information.

21. The method according to claim 19, wherein two or more images of spatial light intensity information are recorded, each of the images being recorded with two or more substantially different modulation means.

22. The method according to claim 19, wherein the parameter to be assessed is location of biological particles in the spatial light intensity image.

23. The method according to claim 22, wherein the location of biological particles in the first spatial light intensity image is used to determine presence of light intensity information in another recorded image of light intensity information associated to biological particles, where the other light intensity information is fluorescence.

24. The method according to claim 22, wherein the location of biological particles is determined by combining information in a first and a second image of spatial light intensity information, where the images are recorded using illumination from the first light source and applying substantially different modulation means for the images, where the images are dark-field and bright-field images.

25. An image cytometer, comprising:
   a first light source configured for emitting light with a wavelength less than 400 nm into a sample region;
   a collimator for forming collimated light from the first light source, the collimator configured to direct the collimated light along an optical axis of the cytometer and into the sample region;
   a second light source comprising a first excitation light source configured for excitation light into the sample region;
   image forming means for forming at least one image of at least part of the sample region on an array of detection elements, the image forming means including a collective objective having a focal plane;
   the sample region being located between the collimator and the array of detection elements;
   an obstruction placed in a path of the light with a wavelength less than 400 nm at the focal plane of the collective objective, the obstruction interchangeable between an aperture or an opaque obstruction;
   wherein the image cytometer is configured to be interchangeable between a bright-field mode, a dark-field mode and a fluorescence mode, in the fluorescence mode, the at least one image being formed in presence of the excitation light being a fluorescence image, in the bright-field mode, the at least one image being formed in presence of the aperture and the light with a wavelength less than 400 nm emitted from the first light source being a bright-field image, and in the dark-field mode, the at least one image being formed in presence of the opaque obstruction and the light with a wavelength less than 400 nm emitted from the first light source being a dark-field image.

* * * * *